US008084039B2

(12) United States Patent
Stinchcomb et al.

(10) Patent No.: US 8,084,039 B2
(45) Date of Patent: Dec. 27, 2011

(54) METHODS AND COMPOSITIONS FOR LIVE ATTENUATED VIRUSES

(75) Inventors: Dan T. Stinchcomb, Fort Collins, CO (US); Jorge E. Osorio, Mount Horeb, WI (US); O'Neil Wiggan, Fort Collins, CO (US)

(73) Assignee: Inviragen, Inc., Fort Collins, CO (US)

( * ) Notice: Subject to any disclaimer, the term of this patent is extended or adjusted under 35 U.S.C. 154(b) by 625 days.

(21) Appl. No.: 12/098,077

(22) Filed: Apr. 4, 2008

(65) Prior Publication Data

US 2008/0248551 A1 Oct. 9, 2008

Related U.S. Application Data

(60) Provisional application No. 60/910,579, filed on Apr. 6, 2007.

(51) Int. Cl.
*A61K 39/12* (2006.01)
*C12N 1/04* (2006.01)
(52) U.S. Cl. .................. 424/204.1; 435/235.1; 435/243

(58) Field of Classification Search ........................ None
See application file for complete search history.

(56) References Cited

U.S. PATENT DOCUMENTS

| | | | |
|---|---|---|---|
| 2005/0255121 | A1 | 11/2005 | Campbell et al. |
| 2005/0276785 | A1 | 12/2005 | Groetzbach et al. |

FOREIGN PATENT DOCUMENTS

| | | | |
|---|---|---|---|
| WO | 2003086433 | A1 | 10/2003 |
| WO | 2003087327 | A2 | 10/2003 |

OTHER PUBLICATIONS

International Search Report and Written Opinion for PCT/US2008/059472, mailed Dec. 16, 2008.
Bhardwaj et al., "Controlled-release delivery system for the alpha-MSH analog melanotan-I using poloxamer 407," J Pharm Sci 1996, 85(9):915-19.
Burke et al., "Formulation, stability, and delivery of live attenuated vaccines for human use," Crit Rev in Therapeutic Drug Carrier Systems 1999, 16(1):1-83.
Coeshott et al., "Pluronic F127-based systemic vaccine delivery systems," Vaccine 2004, 22:2396-2405.
Desai et al., "Evaluation of Pluronic F127-based sustained-release ocular delivery systems for pilocarpine using the albino rabbit eye model," J Pharm Sci 1998, 87(10):1190-1195.
Kabanov et al., "Pluronic block copolymers for overcoming drug resistance in cancer," Adv Drug Delivery Rev 2002, 54:759-779.
Katakam et al., "Use of polaxamer polymers to stabilize recombinant human growth hormone against various processing stresses," Pharmaceutical Dev Technol 1997, 2(2):143-149.
Miyazaki et al., "Percutaneous absorption of indomethacin from Pluronic F127 gels in rats," J Pharm Pharmacol 1995, 47:455-7.
Newman et al., "Design and development of adjuvant-active nonionic block copolymers," J Pharm Sci 1998, 87 (11):1357-62.

Strappe et al., "Delivery of a lentiviral vector in a Pluronic F127 gel to cells of the central nervous system," Eur J Pharm Biopharm 2005, 61:126-33.

Westerink et al., "ProJuvant (Pluronic F127/chitosan) enhances the immune response to intranasally administered tetanus toxoid," Vaccine 2002, 20:711-23.

Chinese Office Action with English Translation, Application No. 200880018784.3, Oct. 27, 2010.

Danish Patent and Trademark Office Singapore Written Opinion, Application No. 200906668-9, Nov. 30, 2010.

New Zealand Examination Report, Application No. 580978, Oct. 14, 2010.

Extended European Search Report, for EP Application No. EP 2 144 99, dated Oct. 6, 2011.

*Primary Examiner* — Stacy B. Chen
(74) *Attorney, Agent, or Firm* — Faegre & Benson LLP

(57) ABSTRACT

Embodiments herein relate to compositions of and methods for live viruses. In certain embodiments, a live, attenuated virus composition includes, but is not limited to, one or more live, attenuated viruses and compositions to reduce inactivation and/or degradation of the live, attenuated virus. In other embodiments, the live, attenuated virus composition may be a vaccine composition. In yet other compositions, a live, attenuated virus composition may include at least one carbohydrate, at least one protein and at least one high molecular weight surfactants for reducing inactivation and/or degradation of the live, attenuated virus.

30 Claims, 9 Drawing Sheets

METHODS AND COMPOSITIONS FOR LIVE ATTENUATED VIRUSES

PRIORITY

This application claims the benefit under 35 USC § 119(e) of provisional U.S. patent application Ser. No. 60/910,579 filed on Apr. 6, 2007, which is incorporated herein in its entirety.

FEDERALLY FUNDED RESEARCH

Embodiments disclosed herein were supported in part by grant number U54 AI-06537-03 from Rocky Mountain Regional Center for Biodefense and Emerging Infectious Diseases and grant number 5 U01 AI070443-01 from National Institutes of Allergy and Infectious Diseases. The U.S. government may have certain rights to practice the subject invention.

FIELD

Embodiments herein relate to compositions and methods for stabilizing live, attenuated viruses. Other embodiments relate to compositions and methods for reducing degradation of live, attenuated viruses. Still other embodiments relate to uses of these compositions in kits for portable applications and methods.

BACKGROUND

Vaccines to protect against viral infections have been effectively used to reduce the incidence of human disease. One of the most successful technologies for viral vaccines is to immunize animals or humans with a weakened or attenuated strain of the virus (a "live, attenuated virus"). Due to limited replication after immunization, the attenuated strain does not cause disease. However, the limited viral replication is sufficient to express the full repertoire of viral antigens and generates potent and long-lasting immune responses to the virus. Thus, upon subsequent exposure to a pathogenic strain of the virus, the immunized individual is protected from disease. These live, attenuated viral vaccines are among the most successful vaccines used in public health.

Ten of the sixteen viral vaccines approved for sale in the U.S. are live, attenuated viruses. Highly successful live viral vaccines include the yellow fever 17D virus, Sabin poliovirus types 1, 2 and 3, measles, mumps, rubella, varicella and vaccinia viruses. Use of the vaccinia virus vaccine to control smallpox outbreaks led to the first and only eradication of a human disease. The Sabin poliovirus vaccine has helped prevent crippling disease throughout the world and is being used in the efforts to eradicate polio. Childhood vaccination with measles, mumps, rubella and varicella vaccines prevent millions of deaths and illnesses internationally.

Recent technical advances, such as reassortment, reverse genetics and cold adaptation, have led to the licensure of live, attenuated viruses for influenza and rotavirus. A number of live, viral vaccines developed with recombinant DNA technologies are in human clinical testing, including vaccines for West Nile disease, dengue fever, malaria, tuberculosis and HIV. These recombinant viral vaccines rely on manipulation of well-characterized attenuated viral vaccines, such as adenovirus, vaccinia virus, yellow fever 17D or the dengue virus, DEN-2 PDK-53. The safe, attenuated viruses are genetically engineered to express protective antigens for other viral or bacterial pathogens. Several recombinant viral vaccines have been approved for animal use, including a canarypox/feline leukemia recombinant virus, a canarypox/canine distemper recombinant virus, a canarypox/West Nile recombinant virus and a yellow fever/West Nile recombinant virus. As a group, the live attenuated virus vaccines are amongst the most successful medical interventions in human history, second only to the advent of antibiotics and hold the promise to improve public health throughout the world.

In order for live, attenuated viral vaccines to be effective, they must be capable of replicating after immunization. Thus, any factors that inactivate the virus can cripple the vaccine. For example, widespread distribution and use of the smallpox vaccine prior to World War II was limited because the virus was inactivated after only a few days at ambient temperatures. In the 1920s, French scientists demonstration that freeze-dried vaccine provided long term stability and techniques for large-scale manufacture of freeze-dried vaccine were developed in the 1940s (see for example Collier 1955). In addition to freeze-drying, various additives have been identified that can help stabilize the viruses in live, attenuated viral vaccines (See for example Burke, Hsu et al 1999). These stabilizers typically include one or more of the following components: divalent cations, buffered salt solutions, chelators, urea, sugars (e.g. sucrose, lactose, trehalose), polyols (e.g., glycerol, mannitol, sorbitol, polyethylene glycol), amino acids, protein hydrolystates (e.g. casein hydrolysate, lactalbumin hydrolysate, peptone), proteins (e.g. gelatin, human serum albumin) or polymers (e.g. dextran).

However, even with these stabilizing agents, many of the commonly used vaccines still require refrigeration for stabilization. Other commonly used vaccines are sensitive to temperature extremes; either excessive heat or accidental freezing can inactivate the vaccine. Maintaining this "cold chain" throughout distribution is particularly difficult in the developing world. Thus, there remains a need for improving the stability of both existing and newly developed live, attenuated viral vaccines.

Flaviviruses are amongst the most labile viruses. They are enveloped viruses with a RNA genome of approximately 11,000 bases. Most of the flaviviruses are transmitted by an arthropod vector, commonly mosquitoes. There are over 70 different flaviviruses that are grouped into three major categories based on serology: the dengue group, the Japanese encephalitis group and the yellow fever group. Amongst the known flaviviruses, 40 are transmitted by mosquitoes, 16 are transmitted by ticks and 18 viruses have no identified insect vector. Thus, most flaviviruses have evolved to replicate in both their arthropod vector and their vertebrate host species (often birds or mammals). Expanding urbanization, worldwide travel and environmental changes (such as deforestation or rain patterns) have lead to the emergence of several flaviviruses as threats to human public health. Such viruses include, but are not limited to, yellow fever virus, the dengue viruses, West Nile virus, Japanese encephalitis virus, and tick-borne encephalitis viruses.

Through intensive mosquito control and vaccination efforts, yellow fever was eliminated from much of North, Central and South America, the Caribbean and Europe. However, in the last 20 years, the number of countries reporting cases has increased. Yellow fever virus is now endemic in major portions of Africa and South America and some Caribbean islands. The World Health Organization (WHO) estimates that 200,000 cases of yellow fever occur annually leading to 30,000 deaths. Since World War II, dengue flaviviruses have spread to tropical and subtropical regions throughout the world and now threaten over 3.5 billion people, about half of the world's population. The WHO estimates that 50-100 million cases of dengue fever occur annually. 500,000 of these are the more severe, life-threatening form of the disease, termed dengue hemorrhagic fever, that leads to more than 25,000 deaths per year. A particularly virulent form of West Nile virus was introduced into the Western hemisphere, presumably by travel, in New York in 1999. The mosquito-transmitted virus infected birds as the primary host, but also caused disease and mortality in humans and horses. West Nile virus spread throughout the United States and into Canada and Mexico. Since its introduction, West Nile virus has caused over 20,000 reported cases of West Nile disease leading to 950 deaths in the United States. Japanese encephalitis virus causes 30,000 to 50,000 cases of neurological disease annually, primarily in eastern and southern Asia. 25-30% of the reported cases are fatal. The tick-borne encephalitis viruses are endemic to parts of Europe and Asia and continue to cause episodic outbreaks affecting thousands of individuals. Related viruses with more limited geographical spread include Kunjin virus (a close relative of West Nile) and Murray Valley encephalitis virus in Australia and New Guinea, St. Louis encephalitis virus in North and South America, the Usutu, Koutango, and Yaonde viruses in Africa, and Cacipacore virus in South American.

Live, attenuated viral vaccines have been developed that are safe and protect against flavivirus diseases, such as yellow fever and Japanese encephalitis. The live, attenuated viral vaccine, 17D, has been widely used to prevent yellow fever. The current flavivirus vaccines are lyophilized in the presence of stabilizers. Nonetheless, the vaccines require storage and shipment at 2-8° C., a requirement that is difficult to achieve in the developing world and more remote regions of developed nations. Furthermore, upon reconstitution, the vaccines rapidly lose potency even when stored at 2-8° C.

The measles vaccine is another example of a labile attenuated virus that is used worldwide to prevent disease. Measles virus is an enveloped, non-segmented negative strand RNA virus of the Paramyxovirus family. Measles is a highly contagious, seasonal disease that can affect virtually every child before puberty in the absence of vaccination. In developing countries, mortality rates in measles-infected children can by as high as 2 to 15%. Indeed, despite efforts to institute worldwide immunization, measles still causes greater than 7,000 deaths in children per year. The measles vaccine is a live, attenuated virus that is manufactured in primary chicken fibroblast cells. The vaccine is stabilized with gelatin and sorbitol and is then lyophilized. The stabilized, lyophilized vaccine has a shelf life of 2 years or more if stored at 2 to 8° C. However, the lyophilized vaccine still requires a cold chain that is difficult to maintain in the developing world. Furthermore, upon reconstitution, the vaccine loses 50% of its potency within 1 hour at room temperature (20 to 25° C.).

Thus, a need exists in the art for improved vaccine formulations.

SUMMARY

Embodiments herein concern methods and compositions to reduce or prevent deterioration or inactivation of a live attenuated virus composition. Certain compositions disclosed can include combinations of components that reduce deterioration of a live attenuated virus. Other embodiments herein concern combinations of excipients that greatly enhance the stability of live attenuated viruses. Yet other compositions and methods herein are directed to reducing the need for lower temperatures (e.g. refrigerated or frozen storage) while increasing the shelf life of aqueous and/or reconstituted live attenuated virus.

In accordance with these embodiments, certain live attenuated viruses are directed to flaviviruses. Some embodiments, directed to compositions, can include, but are not limited to, one or more live, attenuated viruses, such as one or more live, attenuated flaviviruses in combination with one or more high molecular weight surfactants, proteins, and carbohydrates.

Compositions contemplated herein can increase the stabilization and/or reduce the inactivation and/or degradation of a live attenuated virus including, but not limited to, a live attenuated Flavivirus, Togavirus, Coronavirus, Rhabdovirus, Filovirus, Paramyxovirus, Orthomyxovirus, Bunyavirus, Arenavirus, Retrovirus, Hepadnavirus, Pestivirus, Picornavirus, Calicivirus, Reovirus, Parvovirus, Papovavirus, Adenovirus, Herpes virus, or Poxvirus.

Other embodiments concern live, attenuated virus compositions and methods directed to a vaccine compositions capable of reducing or preventing onset of a medical condition caused by one or more of the viruses contemplated herein. In accordance with these embodiments, medical conditions may include, but are not limited to, West Nile infection, dengue fever, Japanese encephalitis, Kyasanur forest disease, Murray valley encephalitis, Alkhurma hemorrhagic fever, St. Louis encephalitis, tick-borne encephalitis, yellow fever and hepatitis C virus infection.

In certain embodiments, compositions contemplated herein can be partially or wholly dehydrated or hydrated. In other embodiments, protein agents contemplated of use in compositions herein can include, but are not limited to, lactalbumin, human serum albumin, a recombinant human serum albumin (rHSA), bovine serum albumin (BSA), other serum albumins or albumin gene family members. Saccharides or polyol agents can include, but are not limited to, monosaccharides, disaccharides, sugar alcohols, trehalose, sucrose, maltose, isomaltose, cellibiose, gentiobiose, laminaribose, xylobiose, mannobiose, lactose, fructose, sorbitol, mannitol, lactitol, xylitol, erythritol, raffinose, amylase, cyclodextrins, chitosan, or cellulose. In certain embodiments, surfactant agents can include, but are not limited to, a non-ionic surfactant such as alkyl poly(ethylene oxide), copolymers of poly(ethylene oxide) and poly(propylene oxide) (EO-PO block copolymers), poly(vinylpyrrolidone), alkyl polyglucosides (such as sucrose monostearate, lauryl diglucoside, or sorbitan monolaureate, octyl glucoside and decyl maltoside), fatty alcohols (cetyl alcohol or olelyl alcohol), or cocamides (cocamide MEA, cocamide DEA and cocamide TEA).

In other embodiments, the surfactants can include, but are not limited to, copolymer poloxamer 407; Pluronic F127®, poloxamer 188; Pluronic F68®, copolymer EO30PO70EO70; Pluronic P123®, or other EO-PO block copolymers of greater than 3,000-4,000 MW.

In some embodiments, vaccine compositions can include, but are not limited to, one or more protein agent that is serum albumin; one or more saccharide agent that is trehalose; and one or more surfactant polymer agent that is the EO-PO block copolymer, copolymer poloxamer 407, Pluronic F127®.

Some embodiments herein concern partially or wholly dehydrated live, attenuated viral compositions. In accordance with these embodiments, a composition may be 20% or more; 30% or more; 40% or more; 50% or more; 60% or more; 70% or more; 80% or more; or 90% or more dehydrated.

Other embodiments concern methods for decreasing inactivation of a live attenuated viruses including, but not limited to, combining one or more live attenuated viruses with a composition capable of reducing inactivation of a live, attenuated virus including, but not limited to, one or more protein agents; one or more saccharides or polyols agents; and one or more high molecular weight surfactants, wherein the composition decreases inactivation of the live attenuated virus. In accordance with these embodiments, the live attenuated virus may include, but is not limited to, a Flavivirus, Togavirus, Coronavirus, Rhabdovirus, Filovirus, Paramyxovirus, Orthomyxovirus, Bunyavirus, Arenavirus, Retrovirus, Hepadnavirus, Pestivirus, Picornavirus, Calicivirus, Reovirus, Parvovirus, Papovavirus, Adenovirus, Herpes virus, or a Poxvirus. Additionally, methods and compositions disclosed herein can include freeze drying or other dehydrating methods for the combination. In accordance with these methods and compositions, the methods and compositions decrease inactivation of the freeze dried or partially or wholly dehydrated live attenuated virus. In other methods, compositions for decreasing inactivation of a live attenuated virus may comprise an aqueous composition or may comprise a rehydrated composition after dehydration. Compositions described herein are capable of increasing the shelf life of an aqueous or rehydrated live attenuated virus.

In certain particular embodiments, a live attenuated virus for use in a vaccine composition contemplated herein may include, but is not limited to, one or more live, attenuated flavivirus vaccines, including but not limited to, attenuated yellow fever viruses (such as 17D), attenuated Japanese encephalitis viruses, (such as SA 14-14-2), attenuated dengue viruses (such as DEN-2/PDK-53 or DEN-4Δ30) or recombinant chimeric flaviviruses.

In certain embodiments, compositions contemplated herein are capable of decreasing inactivation and/or degradation of a hydrated live attenuated virus for greater than 24 hours at room temperatures (e.g. about 20° to about 25° C.) or refrigeration temperatures (e.g. about 0° to about 10° C.). In more particular embodiments, a combination composition is capable of maintaining about 100 percent of the live attenuated virus for greater than 24 hours. In addition, combination compositions contemplated herein are capable of reducing inactivation of a hydrated live attenuated virus during at least 2 freeze and thaw cycles. Other methods concern combination compositions capable of reducing inactivation of a hydrated live attenuated virus for about 24 hours to about 50 days at refrigeration temperatures (e.g. about 0° to about 10° C.). Compositions contemplated in these methods, can include, but are not limited to, one or more protein agent of serum albumin; one or more saccharide agent of trehalose; and one or more EO-PO block copolymer agent of copolymer poloxamer 407, Pluronic F127. In certain embodiments, the live, attenuated virus composition remains at about 100% viral titer after 7 days at approximately 21° C. and about 100% viral titer after 50 days at refrigeration temperatures around 4° C. Other embodiments herein may include live, attenuated virus composition remaining at about 90%, or about 80% viral titer after 7 days at approximately 21° C. and about 90%, or about 80% viral titer after 50 days at refrigeration temperatures around 4° C. Other embodiments contemplated include live, attenuated virus compositions remaining at about 3× to about 10× the concentration of viral titer after several hours (e.g. 20 hours) at approximately 37° C. compared to other compositions known in the art. (see for example, FIGS. 4 and 5). Compositions disclosed herein reduce degradation of the live, attenuated virus when the composition is stored at approximately 37° C.

Other embodiments concern kits for decreasing the inactivation of a live, attenuated virus composition including, but not limited to, a container; and a composition including, but not limited to, one or more protein agents, one or more saccharide or polyol agents, and one or more EO-PO block copolymer agents, wherein the composition decreases inactivation and/or degradation of a live, attenuated virus. In accordance with these embodiments, a kit composition may include one or more protein agents of serum albumin; one or more saccharide agent of trehalose; and one or more EO-PO block copolymer agent. Additionally, a kit contemplated herein may further include one or more live, attenuated viruses including, but not limited to, a Flavivirus, Togavirus, Coronavirus, Rhabdovirus, Filovirus, Paramyxovirus, Orthomyxovirus, Bunyavirus, Arenavirus, Retrovirus, Hepadnavirus, Pestivirus, Picornavirus, Calicivirus, Reovirus, Parvovirus, Papovavirus, Adenovirus, Herpes virus, or Poxvirus. In certain embodiments, compositions herein can include trehalose as a saccharide agent. In accordance with these embodiments, trehalose concentration may be equal to or greater than 5% (w/v). In certain embodiments, compositions herein can include copolymer poloxamer 407, Pluronic F127®. as an EO-PO block copolymer agent. In accordance with these embodiments, copolymer poloxamer 407, Pluronic F127®. concentration may be about 0.1 to about 4 percent (w/v).

In other embodiments, compositions contemplated herein may contain trace amounts or no divalent cations. For example, compositions contemplated herein may have trace amounts or no calcium/magnesium ($Ca^{+2}/Mg^{+2}$).

BRIEF DESCRIPTION OF THE DRAWINGS

The following drawings form part of the instant specification and are included to further demonstrate certain aspects of particular embodiments herein. The embodiments may be better understood by reference to one or more of these drawings in combination with the detailed description presented herein.

DESCRIPTION OF ILLUSTRATIVE EMBODIMENTS

Definitions

Figure 1:
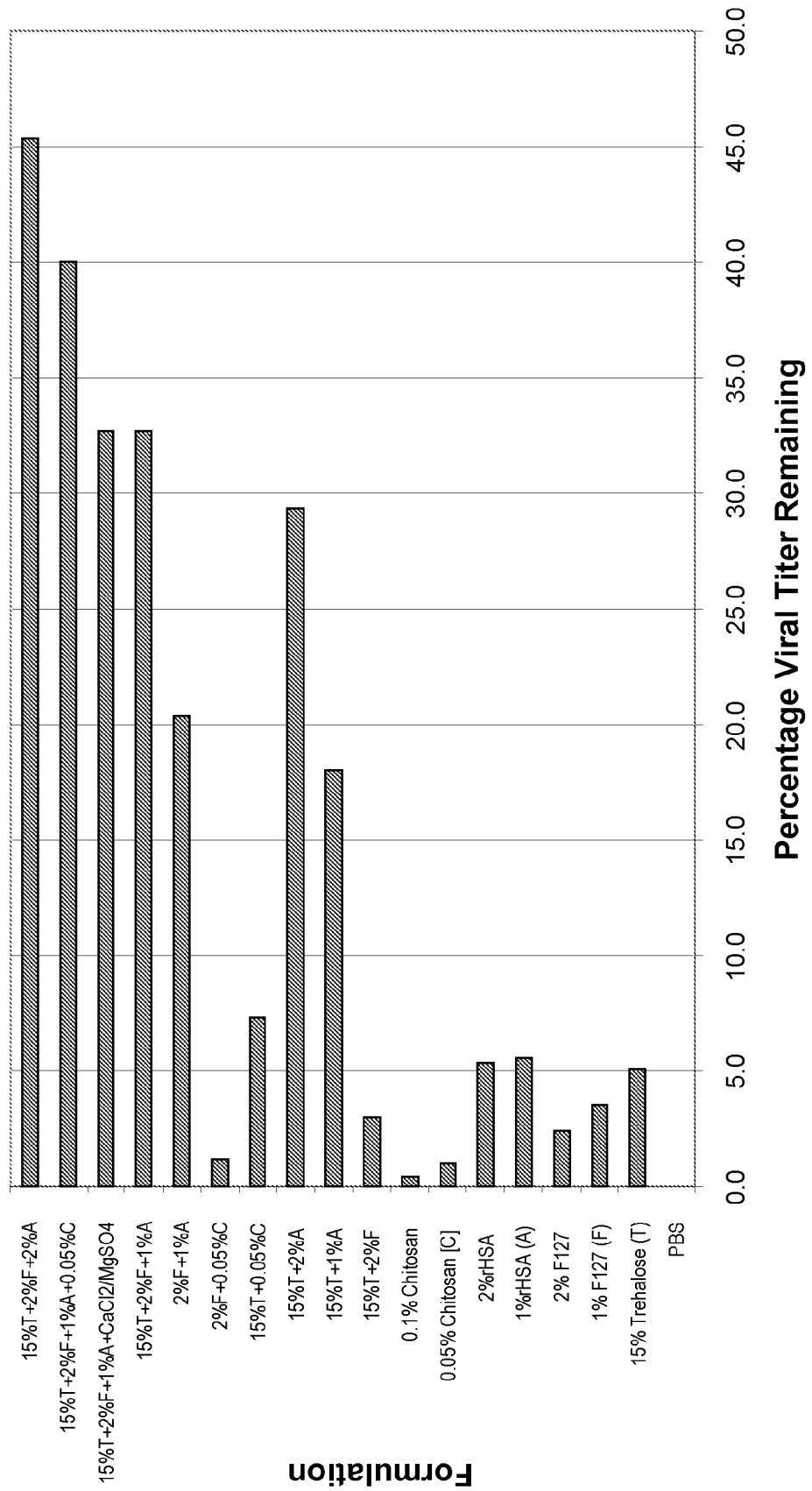
FIG. 1 represents an exemplary histogram of experiments using various compositions for testing the stability of an exemplary virus, DEN-2 PDK 53 flavivirus, in the compositions.

As used herein, "a" or "an" may mean one or more than one of an item.

As used herein, "about" may mean up to and including plus or minus five percent, for example, about 100 may mean 95 and up to 105.

As used herein, "saccharide" agents can mean one or more monosaccharides, (e.g. glucose, galactose, ribose, mannose, rhamnose, talose, xylose, or allose arabinose.), one or more disaccharides (e.g. trehalose, sucrose, maltose, isomaltose, cellibiose, gentiobiose, laminaribose, xylobiose, mannobiose, lactose, or fructose.), trisaccharides (e.g. acarbose, raffinose, melizitose, panose, or cellotriose) or sugar polymers (e.g. dextran, xanthan, pullulan, cyclodextrins, amylose, amylopectin, starch, cellooligosaccharides, cellulose, maltooligosaccharides, glycogen, chitosan, or chitin).

As used herein, "polyol" agents can mean any sugar alcohol (e.g. mannitol, sorbitol, arabitol, erythritol, maltitol, xylitol, glycitol, glycol, polyglycitol, polyethylene glycol, polypropylene glycol, or glycerol). As used herein, "high molecular weight surfactants" can mean a surface active, amphiphilic molecule greater than 1500 molecular weight.

As used herein, "EO-PO block copolymer" can mean a copolymer consisting of blocks of poly(ethylene oxide) and poly(propylene oxide). In addition, as used herein, "Pluronic" can mean EO-PO block copolymers in the EOx-POy-EOx. This configuration of EO-PO block copolymer is also referred to as "Poloxamer" or "Synperonic".

As used herein, "attenuated virus" can mean a virus that demonstrates reduced or no clinical signs of disease when administered to an animal.

DETAILED DESCRIPTIONS

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description.

Stability of flavivirus vaccines has been assessed for both the existing yellow fever and Japanese encephalitis live, attenuated viruses. When tested in 1987, only five of the twelve yellow fever vaccines manufactured at that time met minimal standards of stability. Subsequently, addition of a mixture of sugars, amino acids and divalent cations was demonstrated to stabilize the lyophilized vaccine, so that the vaccine lost less than 1 log of potency after incubation at 37° C. for 14 days. Stabilizing lyophilized formulations for the yellow fever vaccine have been described (see for example U.S. Pat. No. 4,500,512). U.S. Pat. No. 4,500,512, describes a combination of lactose, sorbitol, the divalent cations, calcium and magnesium, and at least one amino acid. While this formulation may help to stabilize the lyophilized vaccine, it fails to provide stability to the vaccine in aqueous form. Another study examined the ability of several different formulations including the compositions described above and the effect of sucrose, trehalose and lactalbumin on the stability of the lyophilized yellow fever vaccine. Formulations consisting of 10% sucrose alone, 2% sorbitol with 4% inositol, or 10% sucrose with 5% lactalbumin, 0.1 g/l $CaCl_2$ and 0.076 g/l $MgSO_4$ were found to provide the best stability (see for example Adebayo, Sim-Brandenburg et al. 1998). However, in all cases after resuspension, yellow fever vaccine is still very unstable and must be discarded after only about one hour (see for example Monath 1996; Adebayo, Sim-Brandenburg et al. 1998). This leads to vaccine wastage and the potential to cause administration of ineffective vaccine under field conditions, if an unstable vaccine is used.

Another live, attenuated flavivirus vaccine for protection against Japanese encephalitis has been licensed and is in widespread use in China (see for example Halstead and Tsai 2004). The Japanese encephalitis vaccine strain, SA 14-14-2, is grown on primary hamster kidney cells and the cell supernatant is harvested and coarsely filtered. One previous composition included 1% gelatin and 5% sorbitol added as stabilizers. Using these stabilizers, the vaccine is lyophilized and then is stable at 2 to 8° C. for at least 1.5 years, but for only 4 months at room temperature and 10 days at 37° C. As with the yellow fever vaccine, the reconstituted vaccine is very labile and is stable for only 2 hours at room temperature (see for example Wanf, Yang et al 1990). In certain embodiments herein, live, attenuated flavivirus compositions for stabilizing or reducing the degradation of Japanese encephalitis are contemplated.

No formulation for a live, attenuated flavivirus vaccine has been identified that provides long term stability of lyophilized formulations at temperatures greater than 2-8° C. In addition, no formulation has been described that prevents loss of titer, stabilizes or reduces degradation of aqueous vaccines for greater than a few hours.

Formulations for other live, attenuated viruses have also been described (see for example Burke, Hsu et al. 1999). One common stabilizer, referred to as SPGA is a mixture of 2 to 10% sucrose, phosphate, potassium glutamate and 0.5 to 2% serum albumin (see for example Bovarnick, Miller et al. 1950). Various modifications of this basic formulation have been identified with different cations, with substitutions of starch hydrolysate or dextran for sucrose, and with substitutions of casein hydrolysate or poly-vinyl pyrrolidone for serum albumin. Other formulations use hydrolyzed gelatin instead of serum albumin as a protein source (Burke, Hsu et al 1999). However, gelatin can cause allergic reactions in immunized children and could be a cause of vaccine-related adverse events. U.S. Pat. No. 6,210,683 describes the substitution of recombinant human serum albumin for albumin purified from human serum in vaccine formulations.

Embodiments herein disclose compositions that enhance the stability of and/or reduce deterioration of live, attenuated virus vaccines compared to those in the prior art. Certain compositions disclosed herein provide stability of aqueous viruses for up to 2 hours; up to 3 hours; up to 4 hours and greater than 4 hours at or about 37° C. Certain compositions disclosed herein provide stability of aqueous viruses for up to 1 day to about 1 week or more, at or about room temperature (e.g. 25° C.). Embodiments contemplated herein provide increased protection of a live, attenuated virus from for example, freezing and/or thawing, and/or elevated temperatures. In certain embodiments, compositions herein can stabilize, reduce deterioration and/or prevent inactivation of dehydrated live, attenuated viral products in room temperature conditions (e.g. about 25° C.). In other embodiments, compositions contemplated herein can stabilize, reduce deterioration and/or prevent inactivation of aqueous live, attenuated viral products at about 25° C. or up to or about 37° C. Compositions and methods disclosed herein can facilitate the storage, distribution, delivery and administration of viral vaccines in developed and under developed regions.

Other embodiments can include compositions for live attenuated virus vaccines including, but not limited to, Picornaviruses (e.g., polio virus, foot and mouth disease virus), Caliciviruses (e.g., SARS virus, and feline infectious peritonitis virus), Togaviruses (e.g., sindbis virus, the equine encephalitis viruses, chikungunya virus, rubella virus, Ross River virus, bovine diarrhea virus, hog cholera virus), Flaviviruses (e.g., dengue virus, West Nile virus, yellow fever virus, Japanese encephalitis virus, St. Louis encephalitis virus, tick-borne encephalitis virus), Coronaviruses (e.g., human coronaviruses (common cold), swine gastroenteritis virus), Rhabdoviruses (e.g., rabies virus, vesicular stomatitis viruses), Filoviruses (e.g., Marburg virus, Ebola virus), Paramyxoviruses (e.g., measles virus, canine distemper virus, mumps virus, parainfluenza viruses, respiratory syncytial virus, Newcastle disease virus, rinderpest virus), Orthomyxoviruses (e.g., human influenza viruses, avian influenza viruses, equine influenza viruses), Bunyaviruses (e.g., hantavirus, LaCrosse virus, Rift Valley fever virus), Arenaviruses (e.g., Lassa virus, Machupo virus), Reoviruses (e.g., human reoviruses, human rotavirus.), Birnaviruses (e.g., infectious bursal virus, fish pancreatic necrosis virus), Retroviruses (e.g., HIV 1, HIV 2, HTLV-1, HTLV-2, bovine leukemia virus, feline immunodeficiency virus, feline sarcoma virus, mouse mammary tumor virus), Hepadnaviruses (e.g., hepatitis B virus), Parvoviruses (e.g., human parvovirus B, canine parvovirus, feline panleukopenia virus) Papovaviruses (e.g., human papillomaviruses, SV40, bovine papillomaviruses), Adenoviruses (e.g., human adenovirus, canine adenovirus, bovine adenovirus, porcine adenovirus), Herpes viruses (e.g., herpes simplex viruses, varicella-zoster virus, infectious bovine rhinotracheitis virus, human cytomegalovirus, human herpesvirus 6), and Poxviruses (e.g., vaccinia, fowlpoxviruses, raccoon poxvirus, skunkpox virus, monkeypoxvirus, cowpox virus, musculum contagiosum virus).

Those skilled in the art will recognize that compositions or formulas herein relate to viruses that are attenuated by any means, including but not limited to, cell culture passage, reassortment, incorporation of mutations in infectious clones, reverse genetics, other recombinant DNA or RNA manipulation. In addition, those skilled in the art will recognize that other embodiments relate to viruses that are engineered to express any other proteins or RNA including, but not limited to, recombinant flaviviruses, recombinant adenoviruses, recombinant poxviruses, recombinant retroviruses, recombinant adeno-associated viruses and recombinant herpes viruses. Such viruses may be used as vaccines for infectious diseases, vaccines to treat oncological conditions, or viruses to introduce express proteins or RNA (e.g., gene therapy, antisense therapy, ribozyme therapy or small inhibitory RNA therapy) to treat disorders.

In some embodiments, compositions herein can contain one or more viruses with membrane envelopes (e.g., enveloped viruses) of the Togavirus, Flavivirus, Coronavirus, Rhabdovirus, Filovirus, Paramyxovirus, Orthomyxovirus, Bunyavirus, Arenavirus, Retrovirus, Hepadnavirus, Herpesvirus or Poxvirus families. In certain embodiments compositions contain one or more enveloped RNA viruses of the Togavirus, Flavivirus, Coronavirus, Rhabdovirus, Filovirus, Paramyxovirus, Orthomyxovirus, Bunyavirus, Arenavirus, or Retrovirus families. In other embodiments, compositions herein can contain one or more enveloped, positive strand RNA virus of the Togavirus, Flavivirus, Coronavirus, or Retrovirus families. In certain embodiments, compositions can contain one or more live, attenuated Flaviviruses (e.g., dengue virus, West Nile virus, yellow fever virus, or Japanese encephalitis virus).

Some embodiments herein relate to compositions for live, attenuated viruses in aqueous or lyophilized form. Those skilled in the art will recognize that formulations that improve thermal viral stability and prevent freeze-thaw inactivation will improve products that are liquid, powdered, freeze-dried or lyophilized and prepared by methods known in the art. After reconstitution, such stabilized vaccines can be administered by a variety routes, including, but not limited to intradermal administration, subcutaneous administration, intramuscular administration, intranasal administration, pulmonary administration or oral administration. A variety of devices are known in the art for delivery of the vaccine including, but not limited to, syringe and needle injection, bifurcated needle administration, administration by intradermal patches or pumps, needle-free jet delivery, intradermal particle delivery, or aerosol powder delivery.

Embodiments can include compositions consisting of one or more live attenuated viruses (as described above) and a mixture of one or more high molecular weight surfactants and one or more proteins in a physiological acceptable buffer. In certain embodiments, compositions include, but are not limited to one or more live attenuated viruses, one or more high molecular weight surfactants, one or more proteins, and one or more carbohydrates, in a physiological acceptable buffer.

In other embodiments, compositions can contain one or more high molecular weight surfactants that increase the thermal stability of live, attenuated viruses. Surfactants have been incorporated into vaccine formulations to prevent material loss to surfaces such as glass vials (see for example Burke, Hsu et al. 1999). However, certain embodiments herein include high molecular weight surfactants with some unusual biochemical properties of utility for compositions and methods disclosed herein. The EO-PO block copolymers can include blocks of polyethylene oxide (—$CH_2CH_2O$— designated EO) and polypropylene oxide (—$CH_2CHCH_3O$— designated PO). The PO block can be flanked by two EO blocks in a $EO_x$-$PO_y$-$EO_x$ arrangement. Since the PO component is hydrophilic and the EO component is hydrophobic, overall hydrophilicity, molecular weight and the surfactant properties can be adjusted by varying x and y in the $EO_x$-$PO_y$-$EO_x$ block structure. In aqueous solutions, the EO-PO block copolymers will self-assemble into micelles with a PO core and a corona of hydrophilic EO groups. EO-PO block copolymer formulations have been investigated as potential drug delivery agents for a variety of hydrophobic drugs and for protein, DNA or inactivated vaccines (e.g. Todd, Lee et al. 1998; Kabanov, Lemieux et al. 2002). At high concentrations (for example: >than 10%) certain of the higher molecular weight EO-PO block copolymers will undergo reverse gelation, forming a gel as the temperature increases. Gel formation at body temperatures permits use of the EO-PO block copolymer gels to act as a depot in drug and vaccine delivery applications (see for example Coeshott, Smithson et al. 2004). In addition, due to their surfactant properties, these polymers have been used in adjuvant formulations, and as an emulsifier in topically applied creams and gels. The EO-PO block copolymers have also been shown to accelerate wound and burn healing and to seal cell membranes after radiation or electroporation-mediated damage.

In other embodiments, vaccine compositions can include one or more surfactants with molecular weight of 1500 or greater. In a certain embodiment, the surfactant is a non-ionic, hydrophilic, polyoxyethylene-polyoxypropylene block copolymer (or EO-PO block copolymer). While EO-PO block copolymers have been used as adjuvants and delivery vehicles for inactivated vaccines, protein vaccines or DNA vaccines, their use to prevent inactivation of a live virus is not anticipated in the art. In a particular embodiment, a formulation can contain one or more EO-PO polymers with a molecular weight of 3,000 or greater. In further embodiments, compositions can include in part an EO-PO block copolymer poloxamer 407, Pluronic F127® or copolymer EO30PO70EO70, Pluronic P123. Those skilled in the art will recognize that modifications of the surfactants can be chemically made. It is contemplated herein any essentially equivalent surfactant polymers are considered.

Embodiments herein can include compositions of one or more live, attenuated viruses, one or more surfactants and one or more proteins. In certain embodiments, a protein can be an albumin. Serum albumin is one of the most common proteins in vertebrate blood and has multiple functions. The protein is 585 amino acids with a molecular weight of 66500. Human serum albumin is not glycosylated and has a single free thiol group implicated in some of its myriad binding activities. Serum albumin is predominantly α-helix with three structural domains, each subdivided into two subdomains. Albumin is known to specifically bind a variety of molecules, including drugs such as aspirin, ibuprofen, halothane, propofol and warfarin as well as fatty acids, amino acids, steroids, glutathione, metals, bilirubin, lysolecithin, hematin, and prostaglandins. The different structural domains are implicated in drug binding; most small molecule drugs and hormones bind to one of two primary sites located in subdomains IIA and IIIA. Due to its lack of immunogenicity, albumin is commonly used as a carrier protein in biological products. Since the protein dose contained in a live, attenuated viral vaccine can be fractions of a microgram (derived from $10^3$ to $10^5$ viral particles), an inert carrier protein is used to prevent loss due to absorption and non-specific binding to glass, plastic or other surfaces. However, as demonstrated herein, an unexpected improvement in stability was observed with the combination of an albumin and EO-PO block copolymers suggesting interactions between the two components and/or between the components and the viral particles. In addition, enhanced stabilization of viruses in the presence of albumin is not likely due to function as a general carrier protein: other proteins such as gelatin and lactoferrin fail to improve virus stability.

In certain embodiments, serum albumin may be from a human or other mammalian source. For vaccines intended for human use, particular embodiments can include human albumin or other human products as needed in order to reduce or eliminate adverse immune responses. Those skilled in the art will recognize that albumins specific for each species may be used in animal vaccines (e.g. canine albumin for canine products, bovine albumin for bovine products). In further embodiments, the protein is a recombinant human albumin. Standard methods exist for expressing recombinant human albumin or portions thereof in a variety of expression systems including bacteria, yeast, algae, plant, mammalian cell or transgenic animal systems. In addition, serum albumin or portions thereof can be produced in cell-free systems or chemically synthesized. Recombinant human albumin produced in these or in any similar system is incorporated herein. Those skilled in the art will recognize that other proteins can substitute for albumin. For example, albumin is a member of a multi-gene family. Due to their structural and sequence similarities, other members of the family (e.g. α-fetoprotein, vitamin D binding protein, or afamin) may substitute for albumin in compositions and methods contemplated herein. Those skilled in the art will also recognize that modifications can be made to albumin by any means known in the art, for example, by recombinant DNA technology, by post-translational modification, by proteolytic cleavage and/or by chemical means. Those substitutions and alterations to albumin that provide essentially equivalent stabilizing function to serum albumin without substitutions and alterations are contemplated herein.

In certain embodiments, compositions having a high molecular weight surfactant, a protein and a carbohydrate in a pharmaceutically acceptable buffer are described. In some embodiments, the carbohydrate is a sugar or a polyol. Sugars can include, but are not limited to, monosaccharides, (e.g. glucose, galactose, ribose, mannose, rhamnose, talose, xylose or allose arabinose), disaccharides (e.g. trehalose, sucrose, maltose, isomaltose, cellibiose, gentiobiose, laminaribose, xylobiose, mannobiose, lactose, or fructose.), trisaccharides (e.g. acarbose, raffinose, melizitose, panose, or cellotriose) or sugar polymers (e.g. dextran, xanthan, pullulan, cyclodextrins, amylose, amylopectin, starch, celloologosaccharides, cellulose, maltooligosaccharides, glycogen, chitosan, or chitin). Polyols can include, but are not limited to, mannitol, sorbitol, arabitol, erythritol, maltitol, xylitol, glycitol, glycol, polyglycitol, polyethylene glycol, polypropylene glycol, and glycerol.

In a particular embodiment, formulations can contain a combination of one or more EO-PO block copolymers, one or more proteins, and trehalose in a pharmacologically acceptable buffer. In certain embodiments, trehalose can be present at concentrations ranging from 5 to 50% (w/v). Trehalose has been used to enhance the stability of protein formulations. It is widely known in the art as a cryopreservative and is used in nature to protect organisms from stress. Anhydrobiotic organisms that can tolerate low water conditions contain large amounts of trehalose. Trehalose has been shown to prevent both membrane fusion events and phase transitions that can cause membrane destabilization during drying. Structural analysis suggests that trehalose fits well between the polar head groups in lipid bylayers. Trehalose also prevents denaturation of labile proteins during drying. It is thought that trehalose stabilizes proteins by hydrogen bonding with polar protein residues. Trehalose is a disaccharide consisting of two glucose molecules in a 1:1 linkage. Due to the 1:1 linkage, trehalose has little or no reducing power and is thus essentially non-reactive with amino acids and proteins. This lack of reducing activity may improve the stabilizing affect of trehalose on proteins. In certain embodiments, trehalose provides stability to live, attenuated viruses. This activity of trehalose may be due to its ability to stabilize both the membranes and coat proteins of the viruses.

In further embodiments, compositions can include one or more EO-PO block copolymers, one or more proteins and one or more carbohydrates, where one of the carbohydrates is chitosan, in a physiological acceptable buffer to provide improved stability to live, attenuated viruses. In certain embodiments, compositions can include chitosan at concentrations ranging from 0.001 to 2% (e.g at a pH of about 6.8). Chitosan is a cationic polysaccharide derived by deacetylation of chitin, the structural polymer of crustacean exoskeletons. It is a polymer of N-acetyl-glucosamine and glucosamine; the content of the two carbohydrates depends on the extent of deacetylation. Chitosan's positive charge allows it to bind to negatively charged surfaces and molecules. Thus, it binds musosal surfaces and is thought to promote mucosal absorption. Chitosan also can bind and form nanoparticles with DNA, RNA and other oligonucleotides and has been used in non-viral gene delivery. Certain embodiments herein demonstrate that chitosan increases live, attenuated virus stability.

In certain embodiments, compositions can be described that typically include a physiologically acceptable buffer. Those skilled in the art recognize that a variety of physiologically acceptable buffers exist, including, but not limited to buffers containing phosphate, TRIS, MOPS, HEPES, bicarbonate, other buffers known in the art ad combinations of buffers. In addition, those skilled in the art recognize that adjusting salt concentrations to near physiological levels (e.g., saline or 0.15 M total salt) may be optimal for parenteral administration of compositions to prevent cellular damage and/or pain at the site of injection. Those skilled in the art also will recognize that as carbohydrate concentrations increase, salt concentrations can be decreased to maintain equivalent osmolarity to the formulation. In certain embodiments, a buffering media with pH greater than 6.8 is contemplated; some live, attenuated viruses (e.g. flaviviruses) are unstable at low pH. In another embodiment, physiologically acceptable buffer can be phosphate-buffered saline (PBS).

Some live, attenuated viral vaccine compositions herein concern compositions that increase stability and/or reduce deterioration of live, attenuated virus in addition to having reduced immunogenicity or are non-immunogenic. In accordance with these embodiments, compositions can include one or more protein agents; one or more saccharides or polyols agents; and one or more high molecular weight surfactants, wherein the composition decreases inactivation of the live attenuated virus. Therefore, certain compositions contemplated herein have reduced adverse reaction when administered to a subject. In some exemplary compositions, the surfactant agent(s) consists of one or more EO-PO block copolymers; the protein agent(s) are selected from the group consisting of lactalbumin, serum albumin, α-fetoprotein, vitamin D binding protein, afamin derived from a vertebrate species; and the carbohydrate agent(s) is one or more of a saccharide and/or a polyol. In certain embodiments, compositions can include one or more of the carbohydrate agent(s) selected from the group consisting of trehalose, sucrose, chitosan, sorbitol, and mannitol. In certain more particular embodiments, in order to reduce immune reaction to a vaccine, the serum albumin can be derived from a vertebrate species or in other embodiments, from the same source as the subject (e.g. human). In other embodiments, the carbohydrate agent is trehalose. In certain embodiments, at least one surfactant agent is the EO-PO block copolymer copolymer poloxamer 407, Pluonic F127®. In some live, attenuated viral vaccine compositions at least one carbohydrate agent is trehalose. In certain live, attenuated viral vaccine compositions include, the EO-PO block copolymer poloxamer 407, Pluronic F127 ® where the concentration is from 0.1 to 4% (w/v); and/or serum albumin concentration from 0.001 to 3% (w/v) and/or the trehalose concentration can be from 5 to 50% (w/v).

Pharmaceutical Compositions

Embodiments herein provide for administration of compositions to subjects in a biologically compatible form suitable for pharmaceutical administration in vivo. By "biologically compatible form suitable for administration in vivo" is meant a form of the active agent (e.g. live, attenuated virus composition of the embodiments) to be administered in which any toxic effects are outweighed by the therapeutic effects of the active agent. Administration of a therapeutically active amount of the therapeutic compositions is defined as an amount effective, at dosages and for periods of time necessary to achieve a desired result. For example, a therapeutically active amount of a compound may vary according to factors such as the disease state, age, sex, and weight of the individual, and the ability formulations to elicit a desired response in the individual. Dosage regimen may be adjusted to provide the optimum therapeutic response.

In some embodiments, composition (e.g. pharmaceutical chemical, protein, peptide of an embodiment) may be administered in a convenient manner such as subcutaneous, intravenous, by oral administration, inhalation, transdermal application, intravaginal application, topical application, intranasal or rectal administration. In a more particular embodiment, the compound may be orally or subcutaneously administered. In another embodiment, the compound may be administered intravenously. In one embodiment, the compound may be administered intranasally, such as inhalation.

A compound may be administered to a subject in an appropriate carrier or diluent, co-administered with the composition. The term "pharmaceutically acceptable carrier" as used herein is intended to include diluents such as saline and aqueous buffer solutions. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition can be sterile and can be fluid to the extent that easy syringability exists. It may further be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Sterile injectable solutions can be prepared by incorporating active compound in an amount with an appropriate solvent or with one or a combination of ingredients enumerated above, as required, followed by sterilization.

Upon formulation, solutions can be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed for administering compositions herein. These particular aqueous solutions are especially suitable for intravenous, intramuscular, subcutaneous and intraperitoneal administration.

The active therapeutic agents may be formulated within a mixture can include about 0.0001 to 1.0 milligrams, or about 0.001 to 0.1 milligrams, or about 0.1 to 1.0 or even about 1 to 10 gram per dose. Single dose or multiple doses can also be administered on an appropriate schedule for a predetermined situation. In some embodiments, doses can be administered before, during and/or after exposure to a virus contemplated herein.

In another embodiment, nasal solutions or sprays, aerosols or inhalants may be used to deliver the compound of interest. Additional formulations that are suitable for other modes of administration include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1% 2%.

Oral formulations include such normally employed excipients as, for example, pharmaceutical grades of mannitol, lactose, starch, magnesium stearate, sodium saccharine, cellulose, magnesium carbonate and the like. In certain embodiments, oral pharmaceutical compositions can include an inert diluent or assimilable edible carrier, or may be enclosed in hard or soft shell gelatin capsule, or may be compressed into tablets, or may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage can be obtained.

Kits

Further embodiments concerns kits for use with methods and compositions described herein. Compositions and live virus formulations may be provided in the kit. The kits can also include a suitable container, live, attenuated virus compositions detailed herein and optionally one or more additional agents such as other anti-viral agents, anti-fungal or anti-bacterial agents.

The kits may further include a suitably aliquoted composition of use in a subject in need thereof. In addition, compositions herein may be partially or wholly dehydrated or aqueous. Kits contemplated herein may be stored at room temperatures or at refrigerated temperatures as disclosed herein depending on the particular formulation.

The container means of the kits will generally include at least one vial, test tube, flask, bottle, syringe or other container means, into which a composition may be placed, and preferably, suitably aliquoted. Where an additional component is provided, the kit will also generally contain one or more additional containers into which this agent or component may be placed. Kits herein will also typically include a means for containing the agent, composition and any other reagent containers in close confinement for commercial sale. Such containers may include injection or blow-molded plastic containers into which the desired vials are retained.

EXAMPLES

The following examples are included to demonstrate certain embodiments presented herein. It should be appreciated by those of skill in the art that the techniques disclosed in the Examples which follow represent techniques discovered to function well in the practices disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope herein.

Example 1

Base Stability of DEN-2 PDK 53 Flavivirus in Liquid Phase

In one illustrative method, the thermal stability for flaviviruses in liquid phase was investigated. In accordance with this method, the base stability of the DEN-2 PDK 53 parental vaccine vector, stored in phosphate buffered saline (PBS), at different temperatures was determined (Table 1). In one example, $1 \times 10^4$ pfu of DEN-2 PDK 53 virus in a total volume of 0.5 ml PBS was incubated, in 2 ml screw capped vials at either 4° C., room temperature (~21° C.) or 37° C. After 24 hours of incubation viral titer and activity was determined by a Neutral Red agarose overlay plaque titration assay in Vero cells. As illustrated in Table 1, incubation of DEN-2 PDK 53 in PBS at 4° C. results in an average four-fold decrease in viral titer and complete loss in viral activity when incubated at 37° C. for the same period. These results demonstrate the relatively poor stability of the DEN-2 PDK 53 flavivirus in the absence of stabilizing excipients.

TABLE 1

Stability of Den-2 PDK53 virus stored for 24 hours at different temperatures.

| Temperature | Formulation | Percentage Viral Titer Loss |
|---|---|---|
| 4° C. | PBS | 75 |
| ~21° C. | PBS | 78 |
| 37° C. | PBS | 100 |

Example 2

Stabilizing Effects of Compositions

In certain exemplary compositions, pharmaceutically acceptable excipients contemplated herein that aid in thermal stability of live viral vaccines are known in the art. In one exemplary method, PBS was used as a base composition to assess the stabilizing effects of different excipients. In these examples, a stock solution of each excipient was made in PBS and the pH adjusted to approximately 7.1 with NaOH, except for chitosan where the pH of the stock solution was adjusted to approximately 6.8. Excipients were diluted in PBS to the final concentrations indicated (w/v) (Table 2). In accordance with this method, $1 \times 10^4$ pfu of DEN-2 PDK 53 virus, in serum-free medium, was added to 0.5 ml of each composition and stored at 37° C. for 24 hours. Following incubation, viral activity and titer was determined by plaque titration in Vero cells, as described above. As illustrated in Table 2, the stabilizing effects of compositions including a single excipient, at various concentrations comparable to previous experimental examples, was minimal. However, some excipients for example, trehalose and recombinant human serum albumin (rHSA), were more effective than others at stabilizing DEN-2 PDK 53 virus at 37° C. Results of the study represented in Table 2 also revealed that increased stabilizing effects of several excipients, including rHSA and trehalose, can be obtained within certain ranges of concentrations of these excipients. In this particular example, trehalose was more effective at concentrations above 15% (w/v) and copolymer poloxamer 407, Pluonic F127® at concentrations between 0.5 and 3%.

TABLE 2

Effects of different excipients on DEN-2 PDK53 stability when stored at 37° C. for 24 hours

| Formulation | Percentage Viral Titer Loss |
|---|---|
| PBS | 100.0 |
| 10% Sucrose | 99.9 |
| 15% Sucrose | 98.3 |
| 20% Sucrose | 96.4 |
| 25% Sucrose | 93.4 |
| 2% Trehalose | 98.3 |
| 5% Trehalose | 97.0 |
| 10% Trehalose | 93.3 |
| 15% Trehalose | 83.3 |
| 2% Mannitol | 100.0 |
| 5% Mannitol | 100.0 |
| 10% Mannitol | 99.8 |
| 15% Mannitol | 86.7 |
| 5% Sorbitol | 100 |
| 10% Sorbitol | 99.9 |
| 15% Sorbitol | 99.9 |
| 1% Polyvinyl Pyrrolidone | 100.0 |
| 5% Polyvinyl Pyrrolidone | 100.0 |
| 10% Polyvinyl Pyrrolidone | 100.0 |
| 0.2% F127 | 99.6 |
| 0.5% F127 | 99.6 |
| 1% F127 | 99.5 |
| 2% F127 | 99.5 |
| 10% F127 | 99.9 |
| 0.1% rHSA | 91.2 |
| 0.5% rHSA | 95.0 |
| 1.0% rHSA | 89.0 |
| 3.0% rHSA | 89.0 |
| 5.0% rHSA | 97.5 |
| 0.05% Chitosan | 99.0 |
| 0.1% Chitosan | 99.0 |

Example 3

Figure 2:
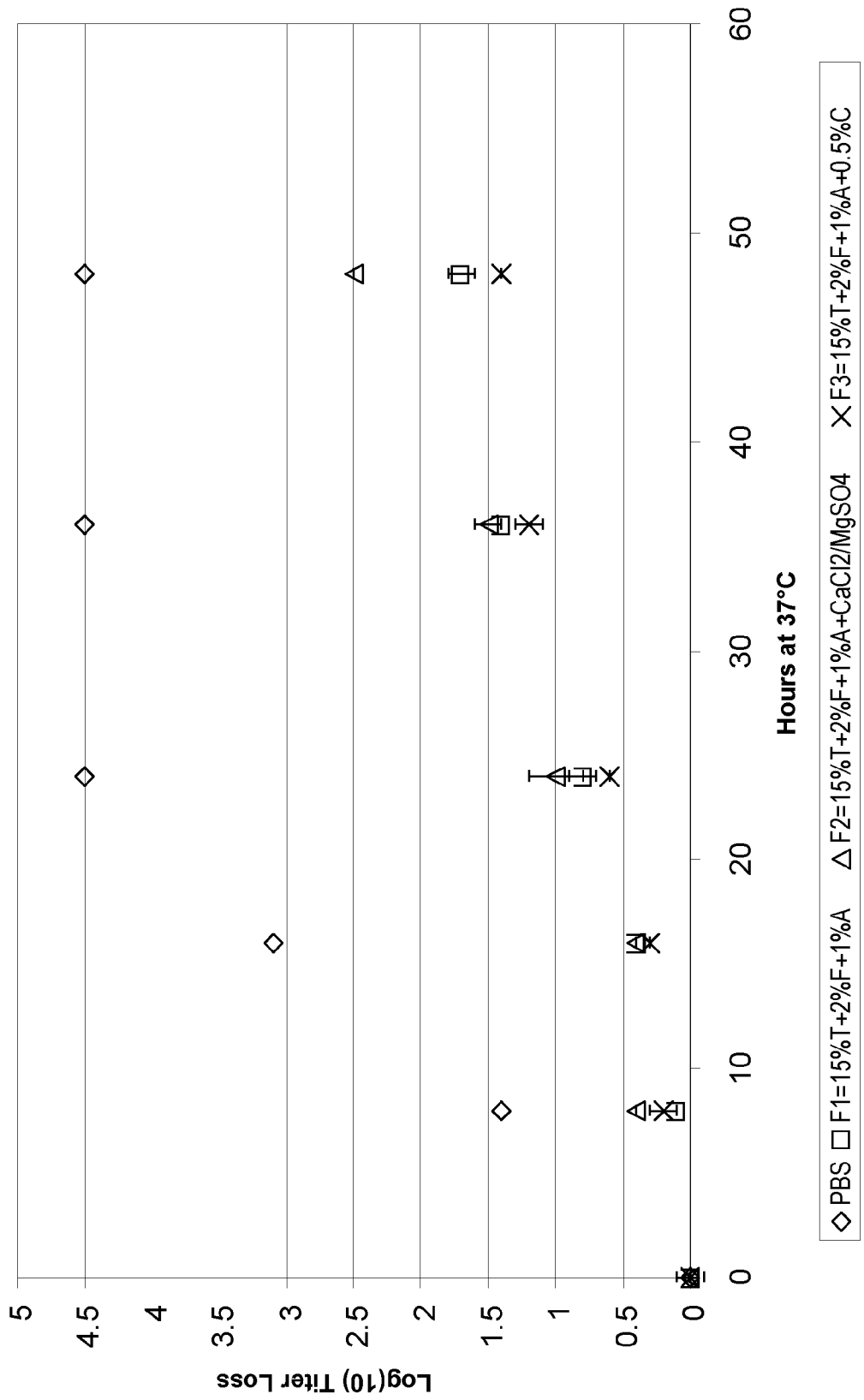
FIG. 2 represents an exemplary graph of a kinetic analysis of an exemplary virus, DEN-2 PDK 53 flavivirus, for viral inactivation at 37° C. in various exemplary compositions.

Stabilizing Effects of Compositions Including Specific Combinations of Excipients In the following illustrative procedure, compositions including multiple excipients in differing combinations and concentrations were tested for stabilizing effects on the parental DEN-2 PDK 53 flaviviral vaccine. Excipients were diluted to the indicated final concentrations in PBS from stock solutions as described in Example 2. $1 \times 10^4$ pfu of DEN-2 PDK 53 vaccine virus was incubated at 37° C. in 0.5 ml of each composition for 21 hours (FIG. 1) or over a 48 hour period (FIG. 2). At the specified time intervals viral titer and activity was determined by a plaque titration assay as described in example 1. FIG. 1 represents exemplary results of this demonstration expressed as percentage of viral titer remaining after incubation, relative to input, and as $\log_{10}$ titer loss in FIG. 2. Analysis of different combinations of excipients, in this particular illustration, revealed that formulations consisting of a saccharide, a pluronic co-polymer non-ionic surfactant and a protein were optimal at improving DEN-2 PDK 53 stability at 37° C. Formulations including trehalose, copolymer poloxamer 407, Pluonic F127® and rHSA had the greatest stabilizing effects. Unexpectedly, the combined stabilizing effect of these three excipients was much greater than the sum of that observed with each individual component suggesting synergism between the components. Improved thermal stability of the DEN-2 PDK 53 flavivirus was obtained through the synergistic activities of the combination of trehalose, copolymer poloxamer 407, Pluonic F127® and rHSA could not have been anticipated based on prior art examples. FIGS. 1 and 2 also illustrate that the stabilizing effect of the trehalose/ copolymer poloxamer 407, Pluonic F127® /rHSA mixture was further enhanced by the addition of 0.05% chitosan. FIG. 2 shows that the rate of viral inactivation when stored over a 48 hour period at 37° C. is significantly reduced by compositions containing trehalose, /copolymer poloxamer 407, Pluonic F127® and rHSA. Examples in the art suggest that the stability of flaviviruses can be enhanced by formulations containing $Ca^{2+}$ and $Mg^{2+}$ divalent cations. However, as represented in FIGS. 1 and 2, the addition of $Ca^{2+}$ (0.0009M) and $Mg^{2+}$ (0.0005M) to a formulation confers no additional stabilizing benefits. The results from FIG. 2 suggest that addition of divalent cations may have a negative impact to long term liquid phase viral stability in the context of particular embodiments.

In one exemplary method, a composition including trehalose, copolymer poloxamer 407, Pluonic F127® and rHSA was assessed for its stabilizing properties with multiple flaviviruses. The stability of chimeric DEN-2 flaviviruses expressing the membrane and envelope proteins from either West Nile (DEN-2/WN), Dengue 1 (DEN-2/D1), Dengue 3 (DEN-2/D3, or Dengue 4 (DEN-2/D4) viruses was determined as described for Example 1. Illustrative results in Table 3 reveal greatly improved liquid phase stability of all the chimeric flaviviruses when stored in a composition including trehalose, copolymer poloxamer 407, Pluonic F127® and rHSA. The different chimeras express different envelope and membrane proteins from five serologically distinct flaviviruses. In addition, West Nile virus and the dengue viruses are significantly divergent. This result suggests that compositions herein may be useful for liquid phase stabilization of diverse members of the family of Flaviviradae as well as other virus families. The ability to stabilize flaviviruses at room temperature (~21° C.) and at 4° C. was examined by representative procedures as outlined for Example 1. The exemplary results, illustrated in Table 4, reveal that a composition including trehalose, copolymer poloxamer 407, Pluonic F127® and rHSA effectively preserves viral activity for 7 days at 21° C. and for 48 days at 4° C.

TABLE 3

Stability of different chimeric flaviviruses stored at 37° C. for 21 hours in PBS or a composition (F1) including 15% trehalose, 2% copolymer poloxamer 407, Pluonic F127 ® and 1% rHSA.

| Virus | Formulation | % Viral Titer Remaining |
|---|---|---|
| DEN-2/WN | PBS | 2 |
|  | F1 | 45 |
| DEN-2/D1 | PBS | 0.2 |
|  | F1 | 22 |
| DEN-2/D3 | PBS | 0.3 |
|  | F1 | 30 |
| DEN-2/D4 | PBS | 1 |
|  | F1 | 28 |

TABLE 4

Stability of flaviviruses stored at different temperatures for 7 or 48 days in PBS or a composition (F1) including 15% trehalose, 2% copolymer poloxamer 407, Pluronic F127 ® and 1% rHSA.

| Virus | Temperature | Formulation | Percentage Viral Titer Remaining | |
|---|---|---|---|---|
| | | | 7 days | 48 days |
| DEN-2 PDK-53 | 21° C. | PBS | 0 | 0 |
| | 21° C. | F1 | 100 | 0 |
| | 4° C. | PBS | 0 | 0 |
| | 4° C. | F1 | 100 | 100 |
| DEN-2/WN | 21° C. | PBS | 0 | 0 |
| | 21° C. | F1 | 100 | 0 |
| | 4° C. | PBS | 0 | 0 |
| | 4° C. | F1 | 100 | 100 |

Example 4

Use of Alternate Components

Figure 3:
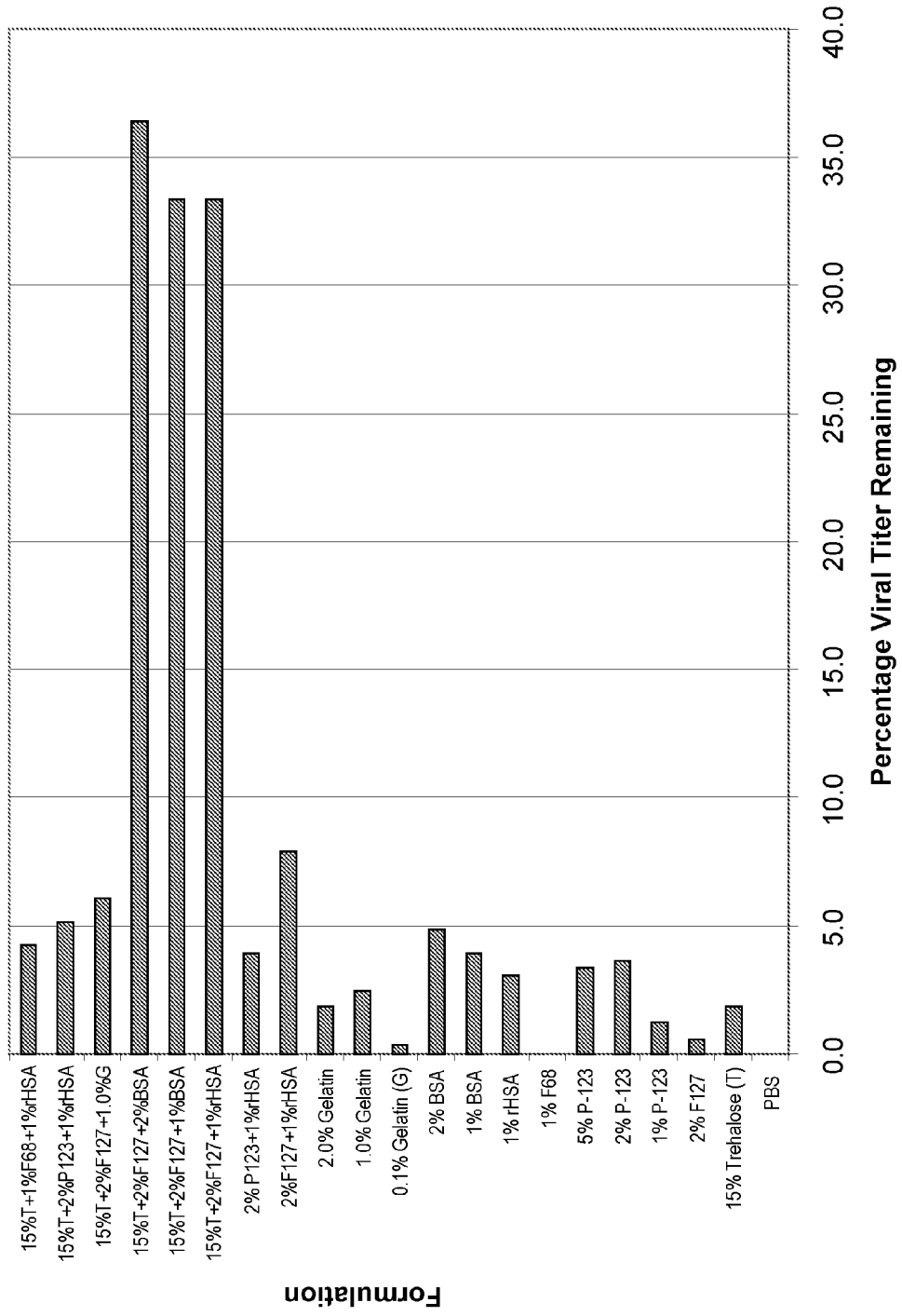
FIG. 3 represents an exemplary histogram of an analysis of an exemplary virus, DEN-2 PDK 53 virus, stored at 37° C. for 21 hours. Values are expressed as a percentage of the viral titer remaining after incubation relative to the input titer. Formulation percentages refer to (w/v) of the respective excipient.

Another exemplary method was used to compare the stabilizing effects of bovine serum albumin (BSA) and, gelatin, to that of rHSA and of different pluronic co-polymers. DEN-2 PDK 53 viral stability assays were conducted as outlined previously for Examples 1 and 2. The previous examples suggested that formulations including trehalose, copolymer poloxamer 407, Pluonic F127® and rHSA optimally improved the thermal stability of the DEN-2 PDK 53 parental vaccine virus. As shown by example in FIG. 3, the stabilizing effects of bovine serum albumin are comparable to those of rHSA either alone or in combination with trehalose and copolymer poloxamer 407, Pluonic F127®. FIG. 3 also demonstrates that as isolated excipients, gelatin is comparable to rHSA in stabilizing DEN-2 PDK 53 at 37° C. However in this exemplary method, unlike BSA, gelatin does not appear to be an effective substitute for rHSA in compositions also containing trehalose and copolymer poloxamer 407, Pluonic F127®. Thus, while proteins other than rHSA may be used in combination with trehalose and copolymer poloxamer 407, Pluonic F127® to aid in stabilization of flaviviral vaccines, the use of a serum albumin or closely related proteins is more suitable in accordance with this exemplary method. In addition, FIG. 3 illustrates that, as isolated excipients, the polymer Pluronic P123 is comparable to copolymer poloxamer 407, Pluonic F127® in its ability to stabilize the DEN-2 PDK-53 virus. However, in this exemplary method, P123 does not appear to be an effective substitute for copolymer poloxamer 407, Pluonic 127® in compositions also containing trehalose and serum albumin. As exemplified in FIG. 4, compositions containing trehalose, rHSA and other commonly used pharmaceutical surfactants such as Polysorbate 20 (Tween 20), instead of a pluronic co-polymer, are not effective in stabilizing DEN-2 PDK 53 relative to formulations containing a pluronic co-polymer. These exemplary methods suggest better stabilizing efficiencies of formulations containing distinct high molecular weight pluronic co-polymer surfactants.

Figure 4:
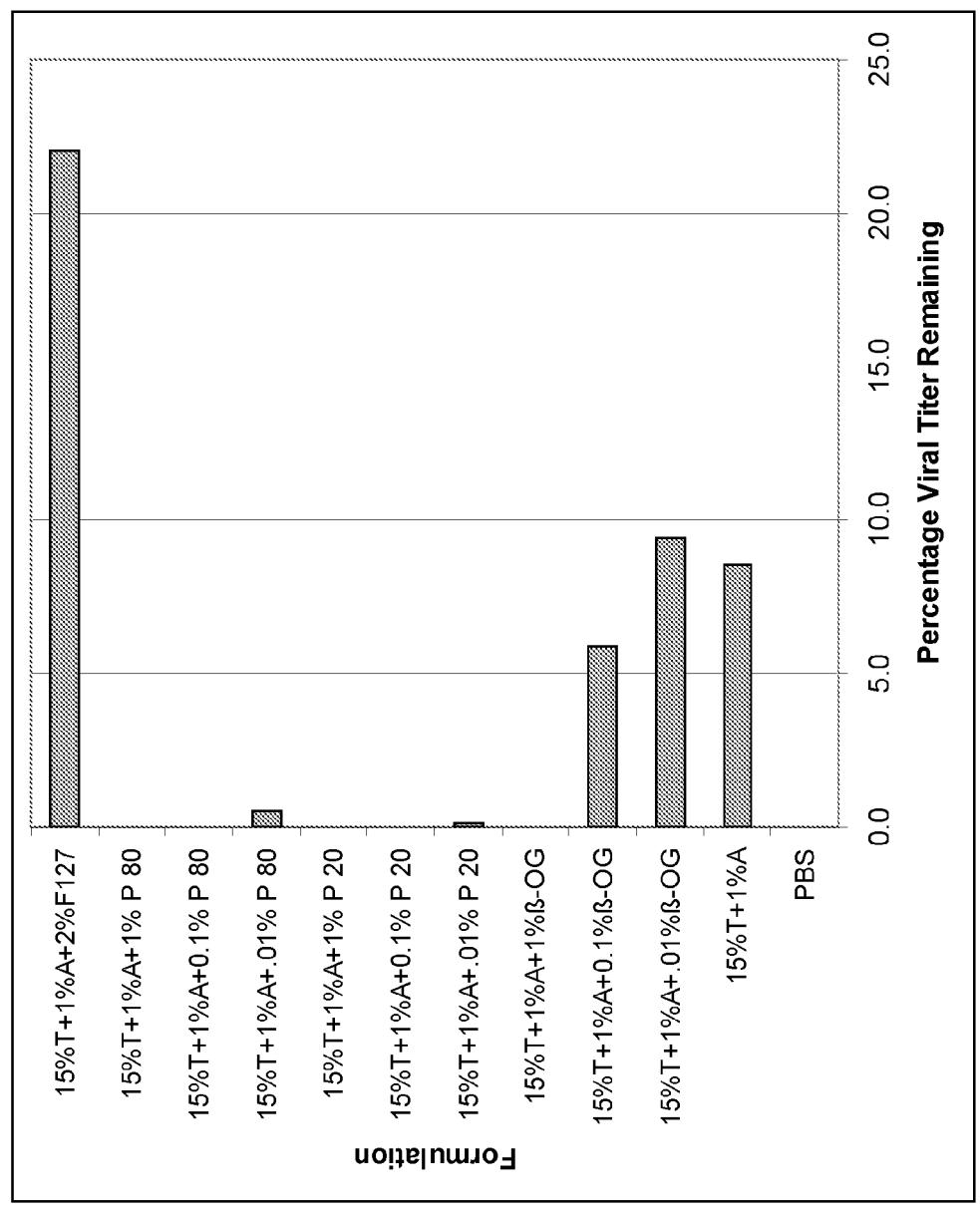
FIG. 4 represents an exemplary histogram of an analysis of an exemplary virus, DEN-2 PDK 53 virus, stored at 37° C. for 23 hours in different compositions. Values are expressed as a percentage of the viral titer remaining after incubation relative to the input titer.

Exemplary data is further illustrated in FIG. 4. FIG. 4. represents stability of the DEN-2 PDK 53 virus in compositions containing different surfactants. DEN-2 PDK 53 was stored at 37° C. for 23 hours in each formulation. Surfactants evaluated in this example include n-octyl-β-D-glucopyranoside (β-OG), Polysorbate 20 (P 20), Polysorbate 80 (P 80) and copolymer poloxamer 407, Pluonic F127® (F). Other formulation components include trehalose (T) and rHSA (A). Values are expressed as a percentage of the viral titer remaining after incubation relative to the input titer.

Example 5

Comparison of the Stabilizing Effects of Different Compositions

Figure 5:
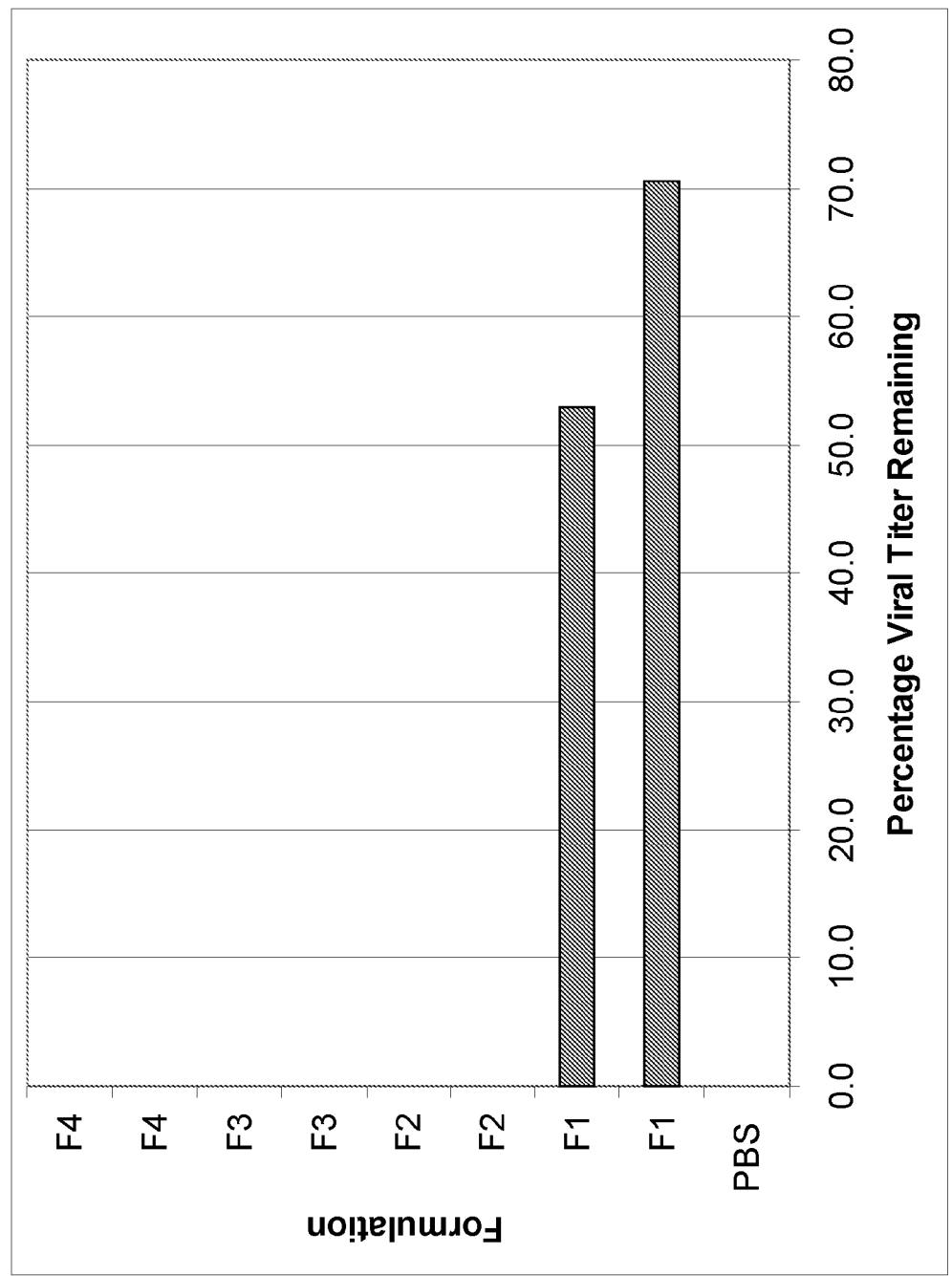
FIG. 5 represents an exemplary histogram of an analysis of an exemplary virus, DEN-2 PDK 53 virus, stored at 37° C. for 23 hours in different compositions. Values are expressed as a percentage of the viral titer remaining after incubation relative to the input titer. The two bars for each formulation represent duplicates in the experiment.

The stabilizing properties of one exemplary composition were compared to that of compositions known in the art. A stabilizing composition for live flaviviral vaccines, disclosed in the art (U.S. Pat. No. 4,500,512), includes 4% lactose, 2% sorbitol, 0.1 g/L $CaCl_2$, 0.076 g/L $MgSO_4$ and amino acids on the order of 0.0005M to 0.05M in PBS. Another composition reported by Adebayo et al (1998) consists of 10% sucrose, 5% lactalbumin, 0.1 g/L $CaCl_2$, and 0.076 g/L $MgSO_4$. In one exemplary method, stabilizing properties of these formulations were compared to a particular embodiment herein. In one example composition, F1, this composition includes 15% trehalose, 2% copolymer poloxamer 407, Pluonic F127® and 1% recombinant HSA. F2 is the formulation of U.S. Pat. No. 4,500,512 without amino acids and F3 is the same formulation with the amino acids histidine and alanine. F4 is the composition of Adebayo, et al. $1 \times 10^4$ pfu of DEN-2 PDK 53 vaccine virus were incubated at 37° C. in 0.5 ml of each composition for 23 hours, after which viral activity and titer was assayed as described in Example 1. As exemplified in FIG. 5, some embodiments, for example formulation F1, represent a significant improvement over those previously described compositions. In the example shown, virtually no viral activity was recovered after storage in the formulations known in the art (formulations F3 and F4), whereas upwards of 50% of the initial viral titer was recovered after storage in a composition disclosed herein. These results reveal that previous formulations are ineffective at promoting live viral vaccine stability during liquid phase storage.

Example 6

Preservation of Viral Activity after Multiple Freeze-Thaws

Figure 6:
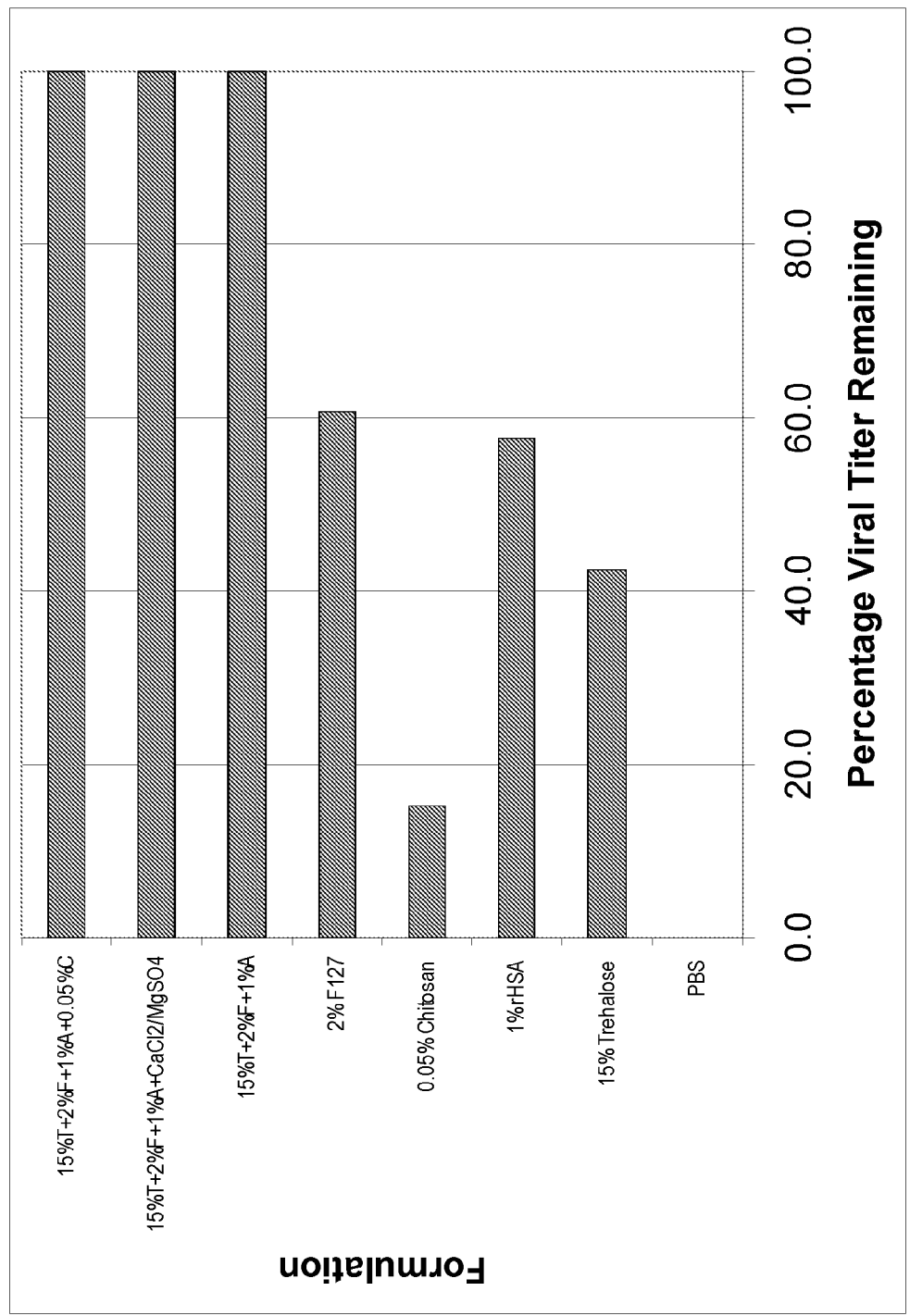
FIG. 6 represents an exemplary histogram analysis of an exemplary virus, DEN-2 PDK 53 virus, after two freeze-thaw cycles when stored in different formulations. Values are expressed as a percentage of the viral titer remaining after freeze-thaw cycles relative to the input titer.

In one exemplary method, the ability of select compositions to preserve viral activity after freeze-thaw cycles was demonstrated. $1 \times 10^4$ pfu of DEN-2 PDK 53 vaccine virus was suspended in 0.5 ml of each composition in screw cap vials. For the first freeze-thaw cycle vials were frozen at −80° C. for 24 hours and thawed rapidly at 37° C. This was immediately followed by a second freeze-thaw cycle where the vials were frozen at −80° C. for 1 hour and thawed rapidly at 37° C. Viral titer and activity was then assessed by a plaque titration assay as described in Example 1. As illustrated in FIG. 6, particular compositions that include trehalose, copolymer poloxamer 407, Pluonic F127® and rHSA effectively preserved full viral activity through two freeze-thaw cycles. Additionally, compositions including these three excipients were more effective than those containing just a single excipient. The results of this particular illustrative experiment suggest the compositions and methods disclosed herein are an effective cryoprotectant for flaviviral vaccines and may facilitate viral preservation during freeze-drying, spray-drying, or other dehydration techniques.

Example 7

Stabilization of Other Live, Attenuated Viruses

Examples illustrated previously reveal effective liquid phase stabilization of several live, attenuated flaviviruses in compositions including trehalose, copolymer poloxamer 407, Pluonic F127® and rHSA. It is anticipated that embodiments disclosed herein may also be effective at stabilizing other live, attenuated viruses. For example, a formulation including trehalose, copolymer poloxamer 407, Pluonic F127® and rHSA may be used to stabilize live attenuated measles virus, an attenuated sindbis virus, an attenuated influenza virus, a recombinant, attenuated adenovirus or a recombinant, attenuated vaccinia virus. In one exemplary method, these non-flaviviral viruses can be suspended and maintained in liquid phase, in a composition including trehalose, copolymer poloxamer 407, Pluonic F127®, and rHSA directly after harvesting from cell culture. In another illustrative method, non-flaviviral viruses can be suspended in a composition prior to, or subsequent to, freeze or spray-drying. Statistically improved viral stability may demonstrate that the formulation of this embodiment is applicable to other attenuated viral vaccines outside of the Flavivirus family. Those skilled in the art recognize that application may then be extended to other live, attenuated viruses.

Example 8

Safety and In Vivo Immunogenicity

Molecular interactions between excipients and molecular or cellular components may serve, not only to enhance stability of viral vaccines, but also to cause increased cell or tissue damage in vivo. The formulations may decrease the immunogenicity of these viral vaccines in live animals. In this example, it is demonstrated that exemplary compositions are safe after subcutaneous injection and are essentially immunologically inert. Four different exemplary compositions were selected for testing in mice as follows.

| Formulation 1: | 15% Trehalose, 2% F-127, 1% rHSA |
|---|---|
| Formulation 2: | 15% Trehalose, 2% F-127, 1% rHSA, 1 mM CaCl$_2$/0.5 mM MgSO$_4$ |
| Formulation 3: | 15% Trehalose, 2% F-127, 1% rHSA, 0.5% chitosan |
| Formulation 4: | 22.5% Trehalose, 3% F-127, 1.5% rHSA |
| Formulation 5: | PBS |

In certain methods described herein, groups of 8 or 9 NIH Swiss mice were immunized by subcutaneous injection with $1 \times 10^5$ pfu of a formulated DEN-2 PDK-53/WN recombinant flavivirus vaccine at day 0 (do), were boosted with the same formulated vaccine at d29 and were then challenged with $10^3$ pfu on a pathogenic West Nile strain (NY99) on d45. Control mice (four groups of 8) received formulations 1-4 alone with no virus. No adverse events after administration in any of the immunized mice were observed. Thus, in this example, no apparent adverse events are caused by the exemplary formulations with or without vaccine virus. Sera were collected prior to immunization at d0, prior to boost at d28, prior to challenge at d44 and post-challenge at d75. West Nile neutralizing antibody titers in the sera were determined by plaque reduction neutralization test (PRNT). The results of the study are represented in Table 5.

TABLE 5

Neutralizing antibody and protection induced by formulated DEN2/WN vaccines

| Formulation | Number | Post-prime (d28) | | Post-boost (d44) | | Post-Challenge (d75) | | Survival | % Survival |
|---|---|---|---|---|---|---|---|---|---|
| | | GMT[1] | % SC[2] | GMT | % SC | GMT | % SC | | |
| 1 | 8 | 30 | 87.5 | 123 | 100 | 761 | 100 | 8/8 | 100 |
| 2 | 8 | 10 | 62.5 | 226 | 100 | 830 | 100 | 8/8 | 100 |
| 3 | 8 | 40 | 100 | 123 | 100 | 1810 | 100 | 8/8 | 100 |
| 4 | 9 | 10 | 66.7 | 137 | 100 | 1660 | 100 | 8/9 | 88.9 |
| 5 | 9 | 10 | 66.7 | 109 | 100 | 1742 | 100 | 9/9 | 100 |
| Controls | 32 | 1 | 0 | 1 | 0 | 1280 | 100 | 7/32 | 21.9 |

[1]GMT = geometric mean titer; titers of <10 were arbitrarily assigned a value of 1.
[2]% SC = percentage of animals that sero-converted with PRNT titers >10.

A majority of the animals receiving the DEN-2/WN vaccine sero-converted after the first dose regardless of whether no formulation (Formulation 5) or one of the exemplary formulations (Formulations 1-4) was used. In addition, all of the vaccinated animals sero-converted after the booster administration. Geometric mean PRNT titers (GMT) demonstrate few differences between the vaccine groups. Titers were low after the primary immunization, increased 3-10 fold after the boost and then showed a dramatic anamnestic response upon challenge. 100% of all the vaccinated animals survived challenge, again independent of vaccine formulation. Only 22% of the control animals survived; those that did survive showed evidence of potent neutralizing antibody responses after challenge. One advantage is that this example demonstrates that the exemplary formulations do not reduce the ability of an exemplary recombinant DEN-2/WN vaccine to prevent West Nile disease in a mice.

Example 9

Figure 7:
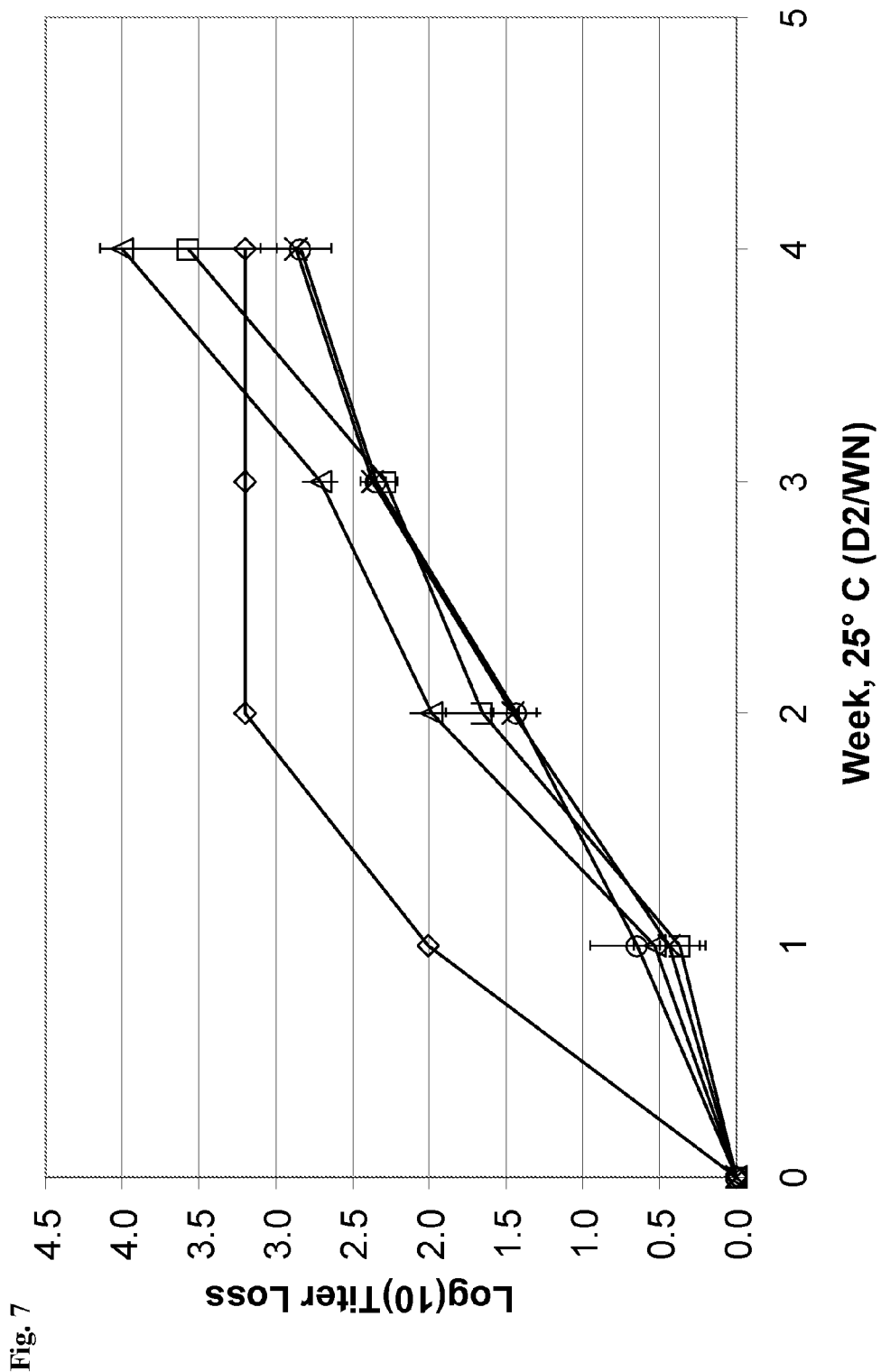
FIG. 7 represents an exemplary graph of a kinetic analysis of an exemplary virus, DEN-2 PDK 53/WN recombinant flavivirus, in various exemplary compositions for viral inactivation at 25° C. over several weeks of time.
Figure 8:
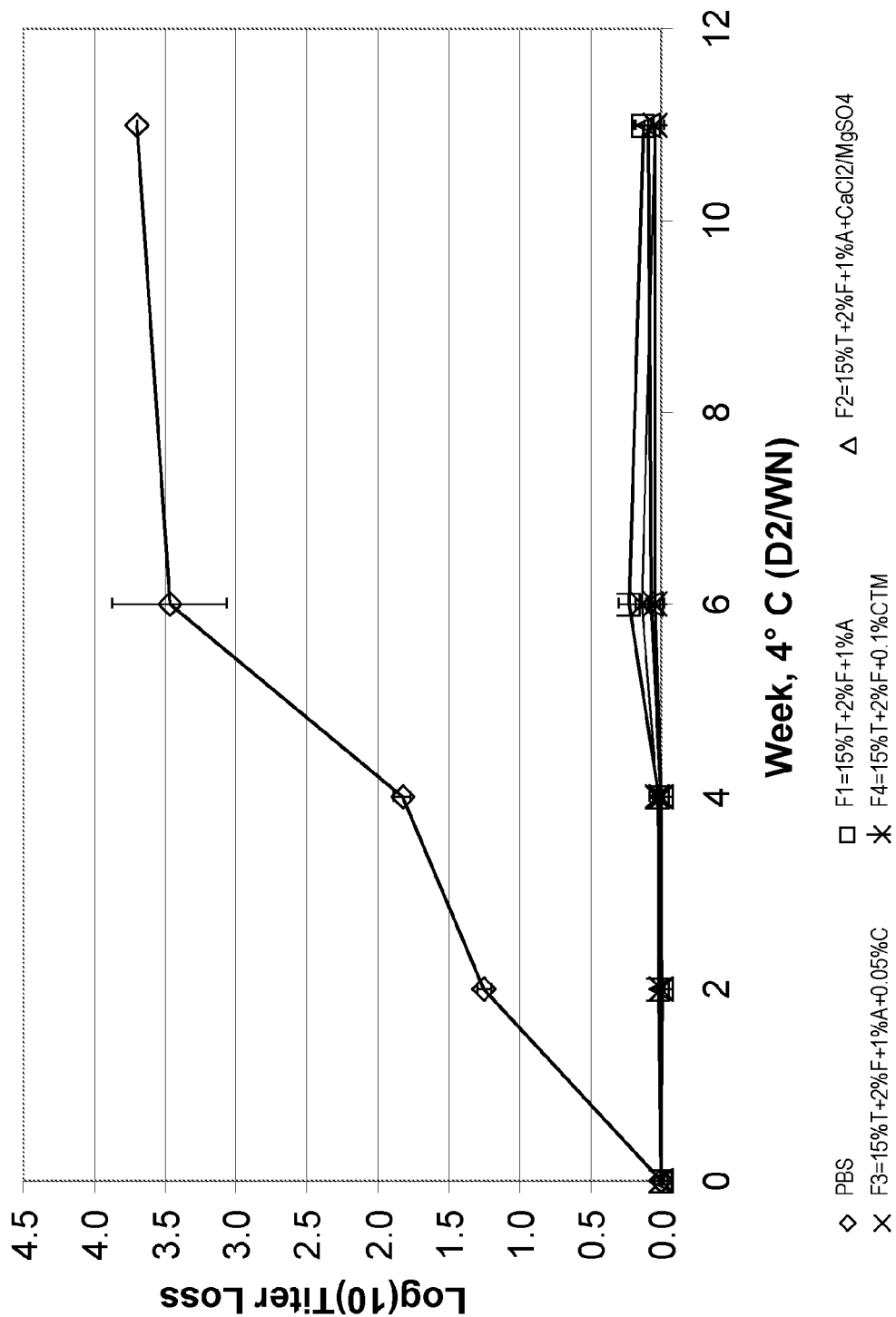
FIG. 8 represents an exemplary graph of a kinetic analysis of an exemplary virus, DEN-2 PDK 53/WN recombinant flavivirus, in various exemplary compositions for viral inactivation at 4° C. over several weeks of time.

In another example, liquid compositions were used containing trehalose, rHSA and copolymer poloxamer 407, Pluonic F127® to stabilize a West Nile chemeric flavivirus stored for various periods at either 25° C. or 4° C. $1 \times 10^4$ pfu of chimeric DEN-2/WN vaccine virus were incubated at each temperature and viral activity was assessed at one or two week intervals as described in Example 1. As illustrated in FIGS. 7 and 8, formulations containing trehalose, rHSA and copolymer poloxamer 407, Pluonic F127® significantly improved the thermal stability of the DEN-2/WN vaccine virus during storage at 25° C. and 4° C., respectively. At 25° C. loss of viral activity was less than one log over 7 days. At 4° C. viral inactivation was negligible for periods up to 12 weeks when stored in exemplary formulations including trehalose, copolymer poloxamer 407, Pluonic F127® and rHSA.

Example 10

Figure 9:
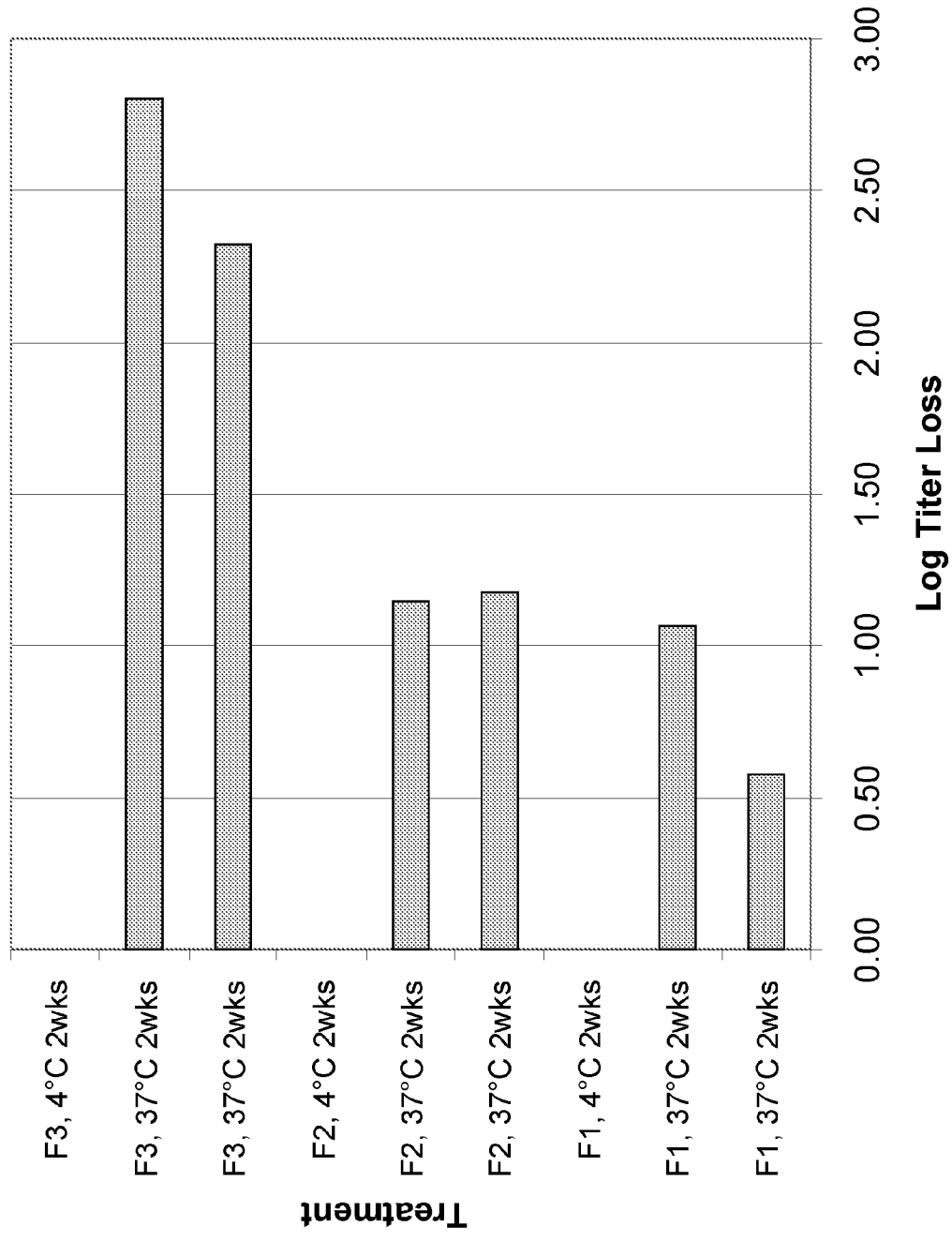
FIG. 9 represents an exemplary histogram analysis of an exemplary virus, DEN-2 PDK-53 virus, after lyophilization in various exemplary compositions. Viral inactivation was assessed as described above after two weeks at different temperatures.

In another exemplary method, stabilizing effects of compositions were demonstrated including trehalose, rHSA and a pluronic co-polymer with dehydrated DEN-2 PDK 53 vaccines. $1 \times 10^4$ pfu of DEN-2 PDK 53 vaccine virus formulated in accordance with procedures disclosed herein. Formulated vaccines were placed in serum vials and subjected to conventional lyophilzation procedures. Dried vaccines were stoppered under vacuum, stored at either 37° C. or 4° C. for 14 days followed by reconstitution of the vaccine to its original liquid volume by addition of sterile water. Viral activity of the reconstituted vaccine was assessed as outlined earlier. At 37° C., in the presence of compositions containing trehalose, rHSA and a pluronic co-polymer formulated in phosphate buffered saline, an average viral titer loss of 1 log was observed (FIG. 9). No loss in viral activity was observed for formulated dehydrated DEN-2 PDK 53 viral vaccines stored at 4° C. for 14 days. These results demonstrate effective preservation of a dehydrated viral vaccine utilizing compositions disclosed herein.

FIG. 9. represents stability of lyophilized DEN-2 PDK 53 at different temperatures. Log titer loss of formulated lyophilized DEN-2 PDK 53 vaccine virus following incubation at 37° C. or 4° C. for 2 weeks as indicated. Formulations F1 (15% trehalose, 2% copolymer poloxamer 407, Pluonic F127®, 1% rHSA) and F2 (15% trehalose, 2% copolymer poloxamer 407, Pluonic F127 ®, 0.01% rHSA) were formulated in phosphate buffered saline. Formulation F3 (15% trehalose, 2% copolymer poloxamer 407, Pluonic F127®, 0.01% rHSA) was formulated in 10 mM Tris base.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

All documents, or portions of documents, cited in this application, including but not limited to patents, patent applications, articles, books, and treatises, are hereby expressly incorporated by reference in their entirety.

What is claimed is:

1. A live attenuated virus composition comprising:
   one or more live, attenuated viruses;
   one or more poly(ethylene oxide) and poly(propylene oxide) (EO-PO) block copolymers, the one or more EO-PO block copolymers include poloxamer 407,
   one or more proteins agents, the one or more protein agents include one or more albumins selected from the group consisting of lactalbumins and serum albumins, and
   one or more carbohydrate agents, the one or more carbohydrate agents include trehalose, wherein the composition is capable of reducing the inactivation of the live attenuated virus.

2. The virus composition of claim 1, wherein the live, attenuated viruses are selected from the group consisting of Flavivirus, Togavirus, Coronavirus, Rhabdovirus, Filovirus, Paramyxovirus, Orthomyxovirus, Bunyavirus, Arenavirus, Retrovirus, Hepadnavirus, Herpesvirus, Poxvirus families and combinations thereof.

3. The virus composition of claim 1, wherein the live, attenuated viruses are Flaviviruses.

4. The virus composition of claim 1, wherein the composition is in aqueous form.

5. The virus composition of claim 1, wherein the composition is partially or wholly dehydrated.

6. The virus composition of claim 1, wherein the one or more albumins include serum albumins derived from a vertebrate species.

7. The virus composition of claim 1, wherein the one or more co-polymers is poloxamer 407, the one or more protein agents is serum albumin, and the one or more carbohydrate agent is trehalose.

8. The virus composition of claim 7, wherein the one or more copolymers concentration is 0.1 to 4% (w/v), wherein the one or more albumins concentration is from 0.001 to 3% (w/v) and the one or more carbohydrates concentration is from 5 to 50% (w/v).

9. A method for decreasing inactivation of a live, attenuated virus composition comprising, combining one or more live attenuated viruses with a composition comprising one or more EO-PO block copolymers, the EO-PO block copolymers include poloxamer 407, one or more proteins agents, the one or more protein agents include one or more albumins selected from the group consisting of lactalbumins and serum albumins; and
   one or more carbohydrate agents, the one or more carbohydrate agents include trehalose, wherein the composition is capable of reducing inactivation of the live, attenuated virus.

10. The method of claim 9, wherein the live, attenuated viruses are selected from the group consisting of Flavivirus, Togavirus, Coronavirus, Rhabdovirus, Filovirus, Paramyxovirus, Orthomyxovirus, Bunyavirus, Arenavirus, Retrovirus, Hepadnavirus, Herpesvirus, Poxvirus families and combinations thereof.

11. The method of claim 9, further comprising partially or wholly dehydrating the combination.

12. The method of claim 11, further comprising partially or wholly re-hydrating the composition prior to administration.

13. The method of claim 9, wherein the composition increases the shelf life of an aqueous virus composition.

14. The method of claim 9, wherein the composition decreases inactivation of an aqueous live, attenuated virus for 24 hours or greater.

15. The method of claim 9, wherein the composition decreases inactivation of an aqueous live, attenuated virus during one or more freeze and thaw cycles.

16. The method of claim 9, wherein the one or more co-polymers is poloxamer 407, the one or more protein agents is serum albumin, and the one or more carbohydrate agent is trehalose.

17. The method of claim 9, wherein the virus composition is administered to a subject to reduce the onset of or prevent a health condition.

18. The method of claim 17, wherein the virus is selected from the group consisting of West Nile, Dengue, Japanese encephalitis, St. Louis encephalitis, Tick-borne encephalitis, and Yellow fever.

19. A kit for decreasing the inactivation of a live, attenuated virus composition comprising:
   at least one container; and
   a composition comprising one or more albumins, the one or more albumins selected from the group consisting of lactalbumins and serum albumins, one or more carbohydrate agents, the one or more carbohydrate agents include trehalose, and one or more EO-PO block copolymers, the EO-PO block copolymers include poloxamer 407.

20. The kit of claim 19, wherein at least one albumin is serum albumin.

21. The kit of claim 19, wherein the trehalose concentration is from 5 to 50% (w/v).

22. The kit of claim 19, wherein the poloxamer 407 concentration is from 0.1 to 4% (w/v).

23. The kit of claim 20, wherein the serum albumin concentration is from 0.001 to 3% (w/v).

24. The kit of claim 19, wherein the composition further comprises one or more live, attenuated viruses.

25. The kit of claim 24, wherein the live, attenuated viruses are selected from the group consisting of Flavivirus, Togavirus, Coronavirus, Rhabdovirus, Filovirus, Paramyxovirus, Orthomyxovirus, Bunyavirus, Arenavirus, Retrovirus, Hepadnavirus, Herpesvirus, Poxvirus families and combinations thereof.

26. A live attenuated virus composition comprising:
one or more live, attenuated viruses;
one or more EO-PO block co-polymers including poloxamer 407; having a concentration of 0.1 to 4% (w/v);

one or more albumins, the one or more albumins selected from the group consisting of lactalbumins and serum albumins; having a concentration from 0.001 to 3% (w/v) and one or more carbohydrate agents, the one or more carbohydrate agent include trehalose, wherein the composition is capable of reducing the inactivation of the live attenuated virus and wherein the composition is in aqueous form.

27. The composition of claim 26, wherein the one or more albumins are serum albumins selected from the group consisting of, bovine serum albumin, canine serum albumin human serum albumin, and other serum albumins.

28. The composition of claim 27, wherein stabilization effects of the agents together are synergistic compared to individual agents.

29. The compositions of claim 27, wherein the composition is a more effective cryoprotectant than its individual agents.

30. The composition of claim 26, wherein the composition is in aqueous form and the composition increases shelf life of the live attenuated virus composition.

* * * * *

UNITED STATES PATENT AND TRADEMARK OFFICE
CERTIFICATE OF CORRECTION

PATENT NO. : 8,084,039 B2
APPLICATION NO. : 12/098077
DATED : December 27, 2011
INVENTOR(S) : Dan T. Stinchcomb et al.

It is certified that error appears in the above-identified patent and that said Letters Patent is hereby corrected as shown below:

In the Specification:

Column 1, lines 13-19 replace paragraph [0002] of the application as filed under FEDERALLY FUNDED RESEARCH with the corrected paragraph below:

"This invention was made with Government support under U54 AI06537 and U01 AI070443 awarded by the National Institutes of Health. The Government has certain rights in this invention."

Signed and Sealed this
Eleventh Day of August, 2015

Michelle K. Lee
*Director of the United States Patent and Trademark Office*